United States Patent
Shi et al.

(10) Patent No.: US 10,081,623 B2
(45) Date of Patent: Sep. 25, 2018

(54) DIAMIDE MACROCYCLES THAT ARE FXIA INHIBITORS

(71) Applicant: BRISTOL-MYERS SQUIBB COMPANY, Princeton, NJ (US)

(72) Inventors: Jun Shi, Pennington, NJ (US); William R. Ewing, Yardley, PA (US); Laura Nielsen, Bartlesville, OK (US); Zilun Hu, Jamison, PA (US); Mimi L. Quan, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/508,122

(22) PCT Filed: Sep. 3, 2015

(86) PCT No.: PCT/US2015/048212
§ 371 (c)(1),
(2) Date: Mar. 2, 2017

(87) PCT Pub. No.: WO2016/036893
PCT Pub. Date: Mar. 10, 2016

(65) Prior Publication Data
US 2017/0283403 A1    Oct. 5, 2017

Related U.S. Application Data

(60) Provisional application No. 62/045,589, filed on Sep. 4, 2014.

(51) Int. Cl.
| | | |
|---|---|---|
| *C07D 401/06* | (2006.01) | |
| *C07D 403/06* | (2006.01) | |
| *C07D 403/12* | (2006.01) | |
| *C07D 409/12* | (2006.01) | |
| *C07D 401/12* | (2006.01) | |

(52) U.S. Cl.
CPC ......... *C07D 409/12* (2013.01); *C07D 401/06* (2013.01); *C07D 401/12* (2013.01); *C07D 403/06* (2013.01); *C07D 403/12* (2013.01)

(58) Field of Classification Search
CPC .. C07D 401/06; C07D 403/06; C07D 403/12; C07D 409/12
See application file for complete search history.

(56) References Cited

U.S. PATENT DOCUMENTS

| | | | |
|---|---|---|---|
| 5,624,936 | A | 4/1997 | deSolms |
| 5,869,682 | A | 2/1999 | deSolms |
| 6,951,840 | B2 | 10/2005 | Belvo et al. |
| 7,544,699 | B2 | 6/2009 | Mjalli et al. |
| 2017/0002006 | A1 | 1/2017 | Corte et al. |
| 2017/0057961 | A1 | 3/2017 | Dilger et al. |

FOREIGN PATENT DOCUMENTS

| | | |
|---|---|---|
| DE | 40 34 829 A1 | 5/1992 |
| EP | 0 525 420 B1 | 5/1999 |
| EP | 1 016 663 A1 | 7/2000 |
| EP | 1 125 925 A1 | 8/2001 |
| FR | 1525186 | 5/1968 |
| FR | 7155 M | 2/1970 |
| GB | 2497806 A | 6/2013 |
| JP | 2015-120685 A | 7/2015 |
| KR | 2015-0136294 A | 12/2015 |
| WO | WO 93/20099 A2 | 10/1993 |
| WO | WO 96/34010 A2 | 10/1996 |
| WO | WO 97/36891 A1 | 10/1997 |
| WO | WO 99/15530 A1 | 4/1999 |
| WO | WO 99/47545 A2 | 9/1999 |
| WO | WO 99/61444 A2 | 12/1999 |
| WO | WO 00/18733 A1 | 4/2000 |
| WO | WO 00/40571 A1 | 7/2000 |
| WO | WO 00/61608 A2 | 10/2000 |
| WO | WO 01/85695 A1 | 11/2001 |

(Continued)

OTHER PUBLICATIONS

U.S. Appl. No. 15/115,314, filed Jul. 29, 2016, Corte et al.
Approaches of Classic Medicinal Chemistry, Optimizing Drug Binding Affinity: (Semi) Empirical Studies, http://www.chem.uzh.ch/zerbe/MedChem/MedChem4_MedChem.pdf (Mar. 18, 2012).
Boger, D.L. et al., "Thermal Atropisomerism of Aglucovancomycin Derivatives: Preparation of (M,M,M)- and (P,M,M)-Aglucovancomycins", J. Am. Chem. Soc., vol. 120, No. 35, pp. 8920-8926 (1998).
Caballero, J. et al., "Quantitative Structure-Activity Relationship Modeling of Growth Hormone Secretagogues Agonist Activity of Some Tetrahydroisoquinoline 1-Carboxamides", Chem. Biol. Drug. Des., vol. 69, pp. 48-55 (2007).

(Continued)

*Primary Examiner* — Bruck Kifle
(74) *Attorney, Agent, or Firm* — Hong Liu

(57) ABSTRACT

The present invention provides compounds of Formula (I) or stereoisomers, tautomers, or pharmaceutically acceptable salts thereof, wherein all the variables are as defined herein. These compounds are selective Factor XIa inhibitors or dual inhibitors of FXIa and plasma kallikrein. This invention also relates to pharmaceutical compositions comprising these compounds and methods of treating thromboembolic and/or inflammatory disorders using the same.

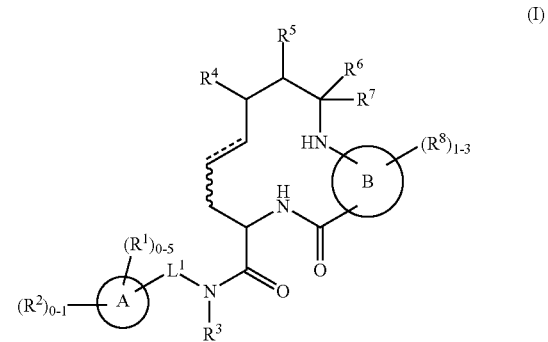

12 Claims, No Drawings

(56) References Cited

FOREIGN PATENT DOCUMENTS

| | | |
|---|---|---|
| WO | WO 02/18369 A2 | 3/2002 |
| WO | WO 03/011222 A2 | 2/2003 |
| WO | WO 03/041641 A2 | 5/2003 |
| WO | WO 03/106438 A1 | 12/2003 |
| WO | WO 2004/080971 A1 | 9/2004 |
| WO | WO 2004/094372 A2 | 11/2004 |
| WO | WO 2005/014533 A2 | 2/2005 |
| WO | WO 2005/099709 A2 | 10/2005 |
| WO | WO 2005/123050 A2 | 12/2005 |
| WO | WO 2005/123680 A1 | 12/2005 |
| WO | WO 2006/017295 A2 | 2/2006 |
| WO | WO 2006/076575 A2 | 7/2006 |
| WO | WO 2006/089005 A2 | 8/2006 |
| WO | WO 2007/047608 A2 | 4/2007 |
| WO | WO 2007/054453 A2 | 5/2007 |
| WO | WO 2007/070816 A2 | 6/2007 |
| WO | WO 2007/070818 A1 | 6/2007 |
| WO | WO 2007/070826 A1 | 6/2007 |
| WO | WO 2007/076431 A1 | 7/2007 |
| WO | WO 2008/076805 A2 | 6/2008 |
| WO | WO 2008/079836 A2 | 7/2008 |
| WO | WO 2008/157162 A1 | 12/2008 |
| WO | WO 2009/114677 A1 | 9/2009 |
| WO | WO 2010/151317 A1 | 12/2010 |
| WO | WO 2011/002520 A1 | 1/2011 |
| WO | WO 2011/017296 A1 | 2/2011 |
| WO | WO 2011/100401 A1 | 8/2011 |
| WO | WO 2011/100402 A1 | 8/2011 |
| WO | WO 2013/009527 A2 | 1/2013 |
| WO | WO 2013/022814 A1 | 2/2013 |
| WO | WO 2013/022818 A1 | 2/2013 |
| WO | WO 2013/055984 A1 | 4/2013 |
| WO | WO 2013/056034 A1 | 4/2013 |
| WO | WO 2013/056060 A1 | 4/2013 |
| WO | WO 2013/093484 A1 | 6/2013 |
| WO | WO 2013/111107 A1 | 8/2013 |
| WO | WO 2013/111108 A1 | 8/2013 |
| WO | WO 2013/118805 A1 | 8/2013 |
| WO | WO 2013/167669 A1 | 11/2013 |
| WO | WO 2013/174937 A1 | 11/2013 |
| WO | WO 2014/014050 A1 | 1/2014 |
| WO | WO 2014/022766 A1 | 2/2014 |
| WO | WO 2014/022767 A1 | 2/2014 |
| WO | WO 2014/059202 A1 | 4/2014 |
| WO | WO 2014/059203 A1 | 4/2014 |
| WO | WO 2014/059214 A1 | 4/2014 |
| WO | WO 2014/108679 A1 | 7/2014 |
| WO | WO 2014/108685 A1 | 7/2014 |
| WO | WO 2014/120346 A1 | 8/2014 |
| WO | WO 2014/154794 A1 | 10/2014 |
| WO | WO 2014/160668 A1 | 10/2014 |
| WO | WO 2015/011087 A1 | 1/2015 |
| WO | WO 2015/044163 A1 | 4/2015 |
| WO | WO 2015/044165 A1 | 4/2015 |
| WO | WO 2015/044167 A1 | 4/2015 |
| WO | WO 2015/044169 A1 | 4/2015 |
| WO | WO 2015/044170 A1 | 4/2015 |
| WO | WO 2015/044172 A1 | 4/2015 |
| WO | WO 2015/044173 A1 | 4/2015 |
| WO | WO 2015/044174 A1 | 4/2015 |
| WO | WO 2015/047973 A1 | 4/2015 |
| WO | WO 2015/054087 A1 | 4/2015 |
| WO | WO 2015/107724 A1 | 7/2015 |
| WO | WO 2015/116882 A1 | 8/2015 |
| WO | WO 2015/116885 A1 | 8/2015 |
| WO | WO 2015/116886 A1 | 8/2015 |
| WO | WO 2015/120062 A2 | 8/2015 |
| WO | WO 2015/120777 A1 | 8/2015 |
| WO | WO 2015/123090 A1 | 8/2015 |
| WO | WO 2015/123091 A1 | 8/2015 |
| WO | WO 2015/123093 A1 | 8/2015 |
| WO | WO 2015/134998 A1 | 9/2015 |
| WO | WO 2015/160634 A1 | 10/2015 |
| WO | WO2015/160636 A1 | 10/2015 |
| WO | WO2015/183709 A1 | 12/2015 |
| WO | WO2016/046157 A1 | 3/2016 |
| WO | WO2016/053455 A1 | 4/2016 |
| WO | WO2016/093285 A1 | 6/2016 |

OTHER PUBLICATIONS

Chan, J.C.Y. et al., "The Characterization of Mice with a Targeted Combined Deficiency of Protein C and Factor XI", American Journal of Pathology, vol. 158, No. 2, pp. 469-479 (2001).

Chen, X. et al., Chapter 32: "The use of bioisosteric groups in lead optimization", Annual Reports in Medicinal Chemistry, vol. 38, pp. 333-346, Elsevier Inc., publ. (2003).

Cho, J.E. et al., "Characterization of Binding Mode for Human Coagulation Factor XI (FXI) Inhibitors", Bull. Korean Chem. Soc., vol. 34, No. 4, pp. 1212-1220 (2013).

Crosby, J.R. et al., "Antithrombotic Effect of Antisense Factor XI Oligonucleotide Treatment in Primates", Arterioscler. Thromb. Vasc. Biol., vol. 33, pp. 1670-1678 (2013), and vol. 33, pp. e127 and e130 (errata) (2013).

Evans, D.A. et al., "Total Syntheses of Vancomycin and Eremomycin Aglycons", Angew. Chem. Int. Ed., vol. 37, No. 19, pp. 2700-2704 (1998).

Gailani, D., "Gene Targeting in Hemostasis, Factor XI", Frontiers in Bioscience, vol. 6, pp. 201-207 (2001).

Gailani, D. et al., "A murine model of factor Xi deficiency", Blood Coagulation and Fibrinolysis, vol. 8, pp. 134-144 (1997).

Gruber, A. et al., "Factor XI-dependence of surface- and tissue factor-initiated thrombus propagation in primates", Blood, vol. 102, No. 3, pp. 953-955 (2003).

Hoffman, M., "A cell-based model of coagulation and the role of factor VIIa", Blood Reviews, vol. 17, pp. S1-S5 (2003).

Jiang, G. et al., "Highly Efficient Oxidation of Amines to Imines by Singlet Oxygen and Its Application in Ugi-Type Reactions", Organic Letters, vol. 11, No. 20, pp. 4568-4571 (2009).

Li, J.J. et al., "Tetrahydroisoquinoline 1-carboxamides as growth hormone secretagogues", Bioorganic & Medicinal Chemistry Letters, vol. 15, pp. 1799-1802 (2005).

Matafonov, A. et al., "Evidence for factor IX-independent roles for factor XIa in blood coagulation", Journal of Thrombosis and Haemostasis, vol. 11, pp. 2118-2127 (2013).

MayoClinic.com, "Pulmonary Embolism: Prevention", http://www.mayoclinic.com/health/pulmonary-embolism/DS00429/DSECTION=prevention, accessed May 20, 2013.

Meijers, J.C.M. et al., "High Levels of Coagulation Factor XI as a Risk Factor for Venous Thrombosis", The New England Journal of Medicine, vol. 342, pp. 696-701 (2000).

Meng, D. et al., "Development of a novel tricyclic class of potent and selective FIXa inhibitors", Bioorganic & Medicinal Chemistry Letters (2015), doi: http://dx.doi.org/10.1016/j.bmcl.2015.07.078.

Minnema, M.C. et al., "Activation of Clotting Factors XI and IX in Patients with Acute Myocardial Infarction", Arterioscler. Thromb. Vasc. Biol., vol. 20, pp. 2489-2493 (2000).

Murakami, T. et al., "Evaluation of Factor XIa-$\alpha_1$-Antitrypsin in Plasma, a Contact Phase-Activated Coagulation Factor-Inhibitor Complex, in Patients with Coronary Artery Disease", Arteriosclerosis, Thrombosis, and Vascular Biology, vol. 15, No. 8, pp. 1107-1113 (1995).

Ngouansavanh, T. et al., "IBX-Mediated Oxidative Ugi-Type Multicomponent Reactions: Application to the N and C1 Functionalization of Tetrahydroisoquinoline", Angew. Chem. Int. Ed., vol. 46, pp. 5775-5778 (2007).

Rosen, E.D. et al., "FXI is Essential for Thrombus Formation Following FeCl$_3$-Induced Injury of the Carotid Artery in the Mouse", Thromb. Haemost., vol. 87, pp. 774-776 (2002).

Schumacher, W.A. et al., "Inhibition of Factor XIa as a New Approach to Anticoagulation", Arterioscler. Thromb. Vasc. Biol., vol. 30, pp. 388-392 (2010).

Schuster, I. et al., "Convenient Synthesis of 1,2,3,4-Tetrahydroisoquinoline-1-Carboxylic Acid Derivatives via Isocyanide-Based Three-Component Reactions", Synthetic Communications, vol. 40, pp. 2488-2498 (2010).

(56) References Cited

OTHER PUBLICATIONS

Schuster, I. et al., "Synthesis of 1,2,3,4-Tetrahydroisoquinoline-1-Carboxylic Acid Derivatives Via Ugi Reactions", Letters in Organic Chemistry, vol. 4, No. 2, pp. 102-108 (2007).

Schuster, I. et al., "Synthesis of 1,2,3,4-Tetrahydroisoquinoline-1-carboxylic Acid Derivatives via Ugi Reactions", Magyar Kémiai Folyóirat (Hungarian Journal of Chemistry), vol. 116, No. 3, pp. 126-130 (2010).

Walsh, P.N., "Platelets and Factor XI Bypass the Contact System of Blood Coagulation", Thrombosis and Haemostasis, vol. 82, No. 2, pp. 234-242 (1999).

Wang, X. et al., "Effects of factor IX or factor XI deficiency on ferric chloride-induced carotid artery occlusion in mice", Journal of Thrombosis and Haemostasis, vol. 3, pp. 695-702 (2005).

Wu, Y.-J. et al., "Discovery of (S,E)-3-(2-fluorophenyl)-N-(1-(3-(pyridin-3-yloxy)phenyl)ethyl)-acrylamide as a potent and efficacious KCNQ2 (Kv7.2) opener for the treatment of neuropathic pain", Bioorganic & Medicinal Chemistry Letters, vol. 23, pp. 6188-6191 (2013).

DIAMIDE MACROCYCLES THAT ARE FXIA INHIBITORS

CROSS REFERENCE TO RELATED APPLICATIONS

This application is a 371 application of PCT/US2015/048212, filed Sep. 3, 2015, which is entitled to priority pursuant to 35 U.S.C. § 119(e) to U.S. provisional patent application No. 62/045,589, filed on Sep. 4, 2014, each of which is fully incorporated herein in its entirety.

FIELD OF THE INVENTION

The present invention relates generally to novel macrocyclic compounds, and their analogues thereof, which are inhibitors of Factor XIa and/or plasma kallikrein, compositions containing them, and methods of using them, for example, for the treatment or prophylaxis of thromboembolic disorders, or for the treatment of retinal vascular permeability associated with diabetic retinopathy and diabetic macular edema.

BACKGROUND OF THE INVENTION

Thromboembolic diseases remain the leading cause of death in developed countries despite the availability of anticoagulants such as warfarin (COUMADIN®), heparin, low molecular weight heparins (LMWH), and synthetic pentasaccharides and antiplatelet agents such as aspirin and clopidogrel (PLAVIX®). The oral anticoagulant warfarin, inhibits the post-translational maturation of coagulation Factors VII, IX, X and prothrombin, and has proven effective in both venous and arterial thrombosis. However, its usage is limited due to its narrow therapeutic index, slow onset of therapeutic effect, numerous dietary and drug interactions, and a need for monitoring and dose adjustment. Thus discovering and developing safe and efficacious oral anticoagulants for the prevention and treatment of a wide range of thromboembolic disorders has become increasingly important.

One approach is to inhibit thrombin generation by targeting the inhibition of coagulation Factor XIa (FXIa). Factor XIa is a plasma serine protease involved in the regulation of blood coagulation, which is initiated in vivo by the binding of tissue factor (TF) to Factor VII (FVII) to generate Factor VIIa (FVIIa). The resulting TF:FVIIa complex activates Factor IX (FIX) and Factor X (FX) that leads to the production of Factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Gailani, D. et al., *Arterioscler. Thromb. Vasc. Biol.*, 27:2507-2513 (2007).) The resulting burst of thrombin converts fibrinogen to fibrin that polymerizes to form the structural framework of a blood clot, and activates platelets, which are a key cellular component of coagulation (Hoffman, M., *Blood Reviews*, 17:S1-S5 (2003)). Therefore, Factor XIa plays a key role in propagating this amplification loop and is thus an attractive target for anti-thrombotic therapy.

Plasma prekallikrein is a zymogen of a trypsin-like serine protease and is present in plasma at 35 to 50 µg/mL. The gene structure is similar to that of Factor XI. Overall, the amino acid sequence of plasma kallikrein has 58% homology to Factor XI. Plasma kallikrein is thought to play a role in a number of inflammatory disorders. The major inhibitor of plasma kallikrein is the serpin C1 esterase inhibitor. Patients who present with a genetic deficiency in C1 esterase inhibitor suffer from hereditary angioedema (HAE) which results in intermittent swelling of face, hands, throat, gastrointestinal tract and genitals. Blisters formed during acute episodes contain high levels of plasma kallikrein which cleaves high molecular weight kininogen liberating bradykinin leading to increased vascular permeability. Treatment with a large protein plasma kallikrein inhibitor has been shown to effectively treat HAE by preventing the release of bradykinin which causes increased vascular permeability (Lehmann, A., "Ecallantide (DX-88), a plasma kallikrein inhibitor for the treatment of hereditary angioedema and the prevention of blood loss in on-pump cardiothoracic surgery", *Expert Opin. Biol. Ther.*, 8:1187-1199 (2008)).

The plasma kallikrein-kinin system is abnormally abundant in patients with advanced diabetic macular edema. It has been recently published that plasma kallikrein contributes to retinal vascular dysfunctions in diabetic rats (Clermont, A. et al., "Plasma kallikrein mediates retinal vascular dysfunction and induces retinal thickening in diabetic rats", *Diabetes*, 60:1590-1598 (2011)). Furthermore, administration of the plasma kallikrein inhibitor ASP-440 ameliorated both retinal vascular permeability and retinal blood flow abnormalities in diabetic rats. Therefore, a plasma kallikrein inhibitor should have utility as a treatment to reduce retinal vascular permeability associated with diabetic retinopathy and diabetic macular edema. Other complications of diabetes such as cerebral hemorrhage, nephropathy, cardiomyopathy and neuropathy, all of which have associations with plasma kallikrein may also be considered as targets for a plasma kallikrein inhibitor.

To date, no small molecule synthetic plasma kallikrein inhibitor has been approved for medical use. The large protein plasma kallikrein inhibitors present risks of anaphylactic reactions, as has been reported for Ecallantide. Thus there remains a need for compounds that inhibit plasma kallikrein, that do not induce anaphylaxis and that are orally available. Furthermore, the molecules in the known art feature a highly polar and ionizable guanidine or amidine functionality. It is well known that such functionalities may be limiting to gut permeability and therefore to oral availability.

SUMMARY OF THE INVENTION

The present invention provides novel macrocyclic compounds, their analogues, including stereoisomers, tautomers, pharmaceutically acceptable salts, or solvates thereof, which are useful as selective inhibitors of serine protease enzymes, especially Factor XIa and/or plasma kallikrein.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of thromboembolic disorders.

The compounds of the invention may be used in the treatment of retinal vascular permeability associated with diabetic retinopathy and diabetic macular edema.

The compounds of the present invention may be used in therapy.

The compounds of the present invention may be used for the manufacture of a medicament for the treatment and/or prophylaxis of a thromboembolic disorder.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

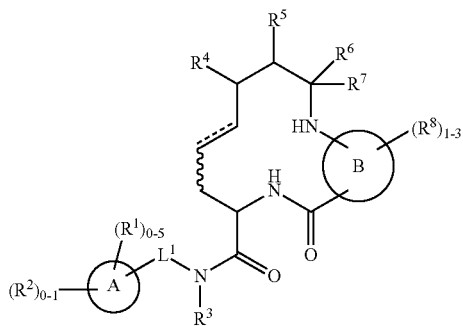

or stereoisomers, tautomers, pharmaceutically acceptable salts, solvates, or prodrugs thereof, wherein:

---- is an optional bond;

ring A is independently selected from a $C_{3-10}$ carbocycle and a 5- to 10-membered heterocycle comprising: carbon atoms and 1-4 heteroatoms selected from N, NH, N($C_{1-4}$ alkyl), NC(=NH)NH$_2$, O, and S;

ring B is independently selected from a aryl and a 5- to 10-membered heterocycle;

$L^1$ is independently selected from a bond, —CR$^5$R$^5$—, —CHR$^5$CHR$^5$—, —CR$^5$=CR$^5$—, —C≡C—, —OCH$_2$—, —CHR$^5$NH—, —CH$_2$O—, —SCH$_2$—, —SO$_2$CH$_2$—, and —CH$_2$NH—;

$R^1$ is, independently at each occurrence, selected from halogen, $C_{1-6}$ alkyl, $C_{1-4}$ alkoxy, $C_{1-4}$ alkylthio, $C_{1-4}$ haloalkyl, OH, =O, OCH$_2$F, OCHF$_2$, OCF$_3$, CF3, CN, NH$_2$, NH($C_{1-4}$ alkyl), N($C_{1-4}$ alkyl)$_2$, CO$_2$($C_{1-4}$ alkyl), CO($C_{1-4}$ alkyl), —CH$_2$NH$_2$, —CONH$_2$, —CONH($C_{1-4}$ alkyl), —OCH$_2$CO$_2$H, —NHCO($C_{1-4}$ alkyl), —NHCO$_2$ ($C_{1-4}$ alkyl), —NHSO$_2$($C_{1-4}$ alkyl), —SO$_2$NH$_2$, and —C(=NH)NH$_2$;

$R^2$ is a 5- to 7-membered heterocycle comprising carbon atoms and 1-4 heteroatoms selected from N, NH, N($C_{1-4}$ alkyl), O, and S(O)$_2$, wherein said heterocycle is substituted with 0-2 $R^{2a}$;

$R^{2a}$ is, independently at each occurrence, selected from halogen, $C_{1-4}$ alkyl, —CH$_2$OH, $C_{1-4}$ alkoxy, OH, CF$_3$, OCF$_3$, OCH$_2$F, OCHF$_2$, CN, NH$_2$, CO$_2$H, CO$_2$($C_{1-4}$ alkyl), COC$_{1-4}$ alkyl, —CONH$_2$, —CONH($C_{1-4}$ alkyl), —CON ($C_{1-4}$ alkyl)$_2$, —SO$_2$($C_{1-4}$ alkyl), —SO$_2$NH$_2$, —SO$_2$NH ($C_{1-4}$ alkyl), and —SO$_2$N($C_{1-4}$ alkyl)$_2$;

$R^3$ is independently selected from H and $C_{1-4}$ alkyl;

alternatively, $L^1$ and $R^3$, together with the nitrogen atom to which they are attached, form a ring;

$R^4$ is selected from H, $C_{1-4}$ alkyl, hydroxyl, F, CF$_3$, and $C_{3-6}$ cycloalkyl;

$R^5$ is selected from H and $C_{1-4}$ alkyl;

$R^6$ is selected from H, halogen, C(O)OH, and C(O)O($C_{1-4}$ alkyl);

$R^7$ is selected from H, $C_{1-4}$ alkyl, and CF$_3$;

alternatively, $R^6$ and $R^7$ together are =O; and $R^8$ is, independently at each occurrence, selected from H, halogen, NHCO$_2$C$_{1-4}$ alkyl, CN, OH, O—$C_{1-4}$ alkyl, CF$_3$, —OCF$_3$, —OCHF$_2$, —CHF$_2$, —CH$_2$F, CO$_2$H, CO$_2$($C_{1-4}$ alkyl), —CH$_2$CO$_2$H, —(CH$_2$)$_2$CO$_2$H, —CH$_2$CO$_2$($C_{1-4}$ alkyl), —(CH$_2$)$_2$CO$_2$($C_{1-4}$ alkyl), NH$_2$, —CH$_2$NH$_2$, —NHCO($C_{1-4}$ alkyl), —NHCO$_2$(CH$_2$)$_{1-2}$O($C_{1-4}$ alkyl), —NHCO$_2$(CH$_2$)$_{1-3}$O($C_{1-4}$ alkyl), NHCO$_2$CH$_2$CH($C_{1-4}$ alkyl)O($C_{1-4}$ alkyl), —NHCO$_2$(CH$_2$)$_{1-2}$OH, —NHCO$_2$CH$_2$CO$_2$H, —CH$_2$NHCO$_2$($C_{1-4}$ alkyl), —NHC (O)NH($C_{1-4}$ alkyl), —NHC(O)N($C_{1-4}$ alkyl)$_2$, NHC(O)NH ($C_{1-4}$ alkyl)N(5- to 6-membered heterocycle), —NHSO$_2$ ($C_{1-4}$ alkyl), —CONH$_2$, —CONH($C_{1-4}$ alkyl), —CON($C_{1-4}$ alkyl)$_2$, and —CH$_2$CONH$_2$.

In another aspect, the present invention provides compounds of Formula (II):

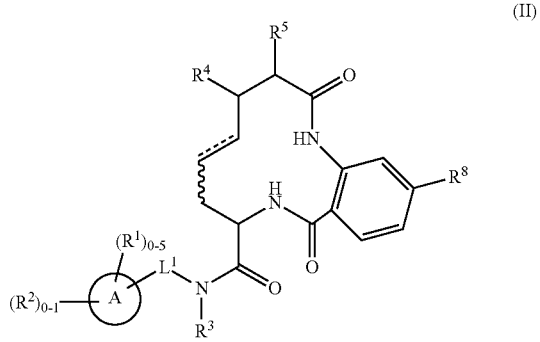

or stereoisomers, tautomers, pharmaceutically acceptable salts, solvates, or prodrugs thereof, wherein:

---- is an optional bond;

ring A is independently selected from a $C_{3-10}$ carbocycle and a 5- to 10-membered heterocycle comprising: carbon atoms and 1-4 heteroatoms selected from N, NH, N($C_{1-4}$ alkyl), NC(=N)NH$_2$, and S;

$L^1$ is independently selected from a bond, —CR$^5$R$^5$—, and —CHR$^5$CHR$^5$—;

$R^1$ is, independently at each occurrence, selected from halogen, $C_{1-6}$ alkyl, $C_{1-4}$ alkoxy, $C_{1-4}$ alkylthio, $C_{1-4}$ haloalkyl, OH, =O, OCH$_2$F, OCHF$_2$, OCF$_3$, CN, NH$_2$, NH($C_{1-4}$ alkyl), N($C_{1-4}$ alkyl)$_2$, CO$_2$($C_{1-4}$ alkyl), CO($C_{1-4}$ alkyl), —CH$_2$NH$_2$, —CONH$_2$, —CONH($C_{1-4}$ alkyl), —OCH$_2$CO$_2$H, —NHCO($C_{1-4}$ alkyl), —NHCO$_2$($C_{1-4}$ alkyl), —NHSO$_2$($C_{1-4}$ alkyl), —SO$_2$NH$_2$, and —C(=NH) NH$_2$;

$R^2$ is a 5- to 7-membered heterocycle comprising carbon atoms and 1-4 heteroatoms selected from N, NH, and N($C_{1-4}$ alkyl);

$R^3$ is independently selected from H and $C_{1-4}$ alkyl;

alternatively, $L^1$ and $R^3$, together with the nitrogen atom to which they are attached, form a ring;

$R^4$ is selected from H, $C_{1-4}$ alkyl, hydroxyl, and $C_{3-6}$ cycloalkyl;

$R^5$ is selected from H and $C_{1-4}$ alkyl; and $R^8$ is independently selected from H, halogen, $NHCO_2C_{1-4}$ alkyl, CN, OH, O—$C_{1-4}$ alkyl, $CF_3$, —$OCF_3$, —$OCHF_2$, —$CHF_2$, —$CH_2F$, $CO_2H$, $CO_2(C_{1-4}$ alkyl), —$CH_2CO_2H$, —$(CH_2)_2CO_2H$, —$CH_2CO_2(C_{1-4}$ alkyl), —$(CH_2)_2CO_2(C_{1-4}$ alkyl), $NH_2$, —$CH_2NH_2$, —$NHCO(C_{1-4}$ alkyl), —$NHCO_2(CH_2)_{1-2}O(C_{1-4}$ alkyl), —$NHCO_2(CH_2)_{1-3}O(C_{1-4}$ alkyl), $NHCO_2CH_2CH(C_{1-4}$ alkyl)$O(C_{1-4}$ alkyl), —$NHCO_2(CH_2)_{1-2}OH$, —$NHCO_2CH_2CO_2H$, —$CH_2NHCO_2(C_{1-4}$ alkyl), —$NHC(O)NH(C_{1-4}$ alkyl), —$NHC(O)N(C_{1-4}$ alkyl)$_2$, $NHC(O)NH(C_{1-4}$ alkyl)N[5- to 6-membered heterocycle)], —$NHSO_2(C_{1-4}$ alkyl), —$CONH_2$, —$CONH(C_{1-4}$ alkyl), —$CON(C_{1-4}$ alkyl)$_2$, and —$CH_2CONH_2$.

In another aspect, the present invention provides compounds of Formula (III):

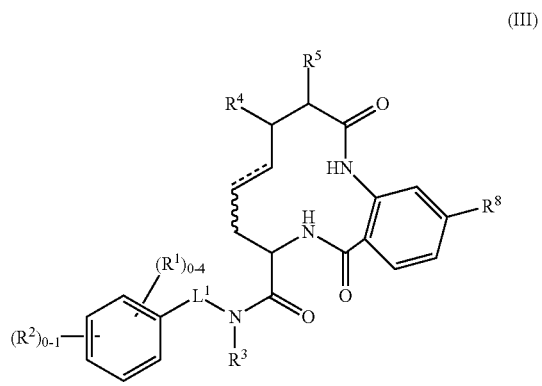

(III)

or stereoisomers, tautomers, pharmaceutically acceptable salts, solvates, or prodrugs thereof, wherein:

---- is an optional bond;

$L^1$ is independently selected from a bond, —$CR^5R^5$—, and —$CHR^5CHR^5$—;

$R^1$ is, independently at each occurrence, selected from halogen, $C_{1-6}$ alkyl, $C_{1-4}$ alkoxy, $C_{1-4}$ alkylthio, $C_{1-4}$ haloalkyl, OH, =O, $OCH_2F$, $OCHF_2$, $OCF_3$, CN, $NH_2$, $NH(C_{1-4}$ alkyl), and $N(C_{1-4}$ alkyl)$_2$;

$R^2$ is a 5- to 7-membered heterocycle comprising carbon atoms and 1-4 heteroatoms selected from N and NH;

$R^3$ is independently selected from H and $C_{1-4}$ alkyl;

$R^4$ is selected from H, $C_{1-4}$ alkyl, hydroxyl, and $C_{3-6}$ cycloalkyl;

$R^5$ is selected from H and $C_{1-4}$ alkyl; and $R^8$ is independently selected from H, halogen, $NHCO_2C_{1-4}$ alkyl, CN, OH, O—$C_{1-4}$ alkyl, $CF_3$, —$OCF_3$, —$OCHF_2$, —$CHF_2$, —$CH_2F$, $CO_2H$, and $CO_2(C_{1-4}$ alkyl).

In another aspect, the present invention provides compounds of Formula (IV):

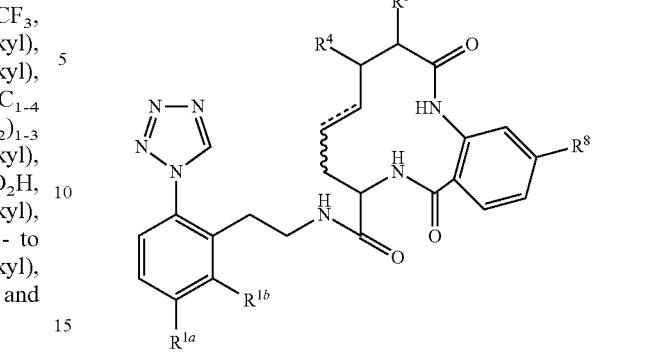

(IV)

or stereoisomers, tautomers, pharmaceutically acceptable salts, solvates, or prodrugs thereof, wherein:

---- is an optional bond;

$R^{1a}$ is selected from H, F, and Cl;

$R^{1b}$ is selected from H and F;

$R^4$ is selected from H, $C_{1-4}$ alkyl, and hydroxyl;

$R^5$ is selected from H and $C_{1-4}$ alkyl; and $R^8$ is independently selected from H, halogen, $NHCO_2C_{1-4}$ alkyl, CN, OH, O—$C_{1-4}$ alkyl, $CF_3$, —$OCF_3$, —$OCHF_2$, —$CHF_2$, —$CH_2F$, $CO_2H$, and $CO_2(C_{1-4}$ alkyl).

In another aspect, the present invention provides compounds of Formula (II), or stereoisomers, tautomers, pharmaceutically acceptable salts, solvates, or prodrugs thereof, wherein:

---- is an optional bond;

ring A is a 5- to 10-membered heterocycle comprising: carbon atoms and 1-4 heteroatoms selected from N, NH, $N(C_{1-4}$ alkyl), and $NC(=NH)NH_2$;

$L^1$ is independently selected from a bond, —$CR^5R^5$—, and —$CHR^5CHR^5$—;

$R^1$ is, independently at each occurrence, selected from halogen, $C_{1-6}$ alkyl, and =O;

$R^3$ is independently selected from H and $C_{1-4}$ alkyl;

$R^4$ is selected from H, $C_{1-4}$ alkyl, hydroxyl, and $C_{3-6}$ cycloalkyl;

$R^5$ is selected from H and $C_{1-4}$ alkyl; and $R^8$ is independently selected from H, halogen, and $NHCO_2C_{1-4}$ alkyl; and other variables are as defined in Formula (II) above.

In another aspect, the present invention provides compounds of Formula (II), or stereoisomers, tautomers, pharmaceutically acceptable salts, solvates, or prodrugs thereof, wherein:

$L^1$ is independently selected from a bond, —CH—, and —$CH_2CH_2$—;

ring A is a 5- to 10-membered heterocycle selected from

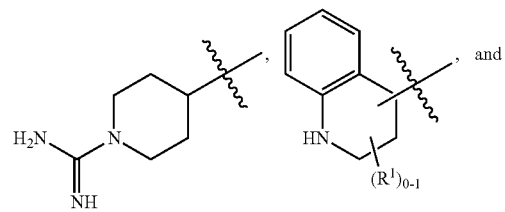

-continued

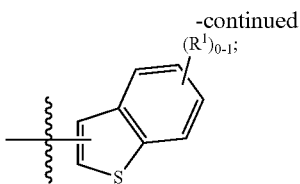

and

R¹ is, independently at each occurrence, selected from halogen and =O; and other variables are as defined in Formula (II) above.

In another aspect, the present invention provides compounds of Formula (II), or stereoisomers, tautomers, pharmaceutically acceptable salts, solvates, or prodrugs thereof, wherein:

---- is an optional bond;

ring A is phenyl;

R¹ is, independently at each occurrence, selected from halogen, $C_{1-6}$ alkyl, $C_{1-4}$ alkoxy, $C_{1-4}$ haloalkyl, and OH;

L¹ and R³, together with the nitrogen atom to which they are attached, form a ring;

R⁴ is selected from H, $C_{1-4}$ alkyl, hydroxyl, and $C_{3-6}$ cycloalkyl;

R⁵ is selected from H and $C_{1-4}$ alkyl; and

R⁸ is independently selected from H, halogen, and $NHCO_2C_{1-4}$ alkyl; and other variables are as defined in Formula (II) above.

In another aspect, the present invention provides a compound selected from any subset list of compounds exemplified in the present application.

In another embodiment, the compounds of the present invention have Factor XIa or plasma kallikrein Ki values ≤10 μM.

In another embodiment, the compounds of the present invention have Factor XIa or plasma kallikrein Ki values ≤1 μM.

In another embodiment, the compounds of the present invention have Factor XIa or plasma kallikrein Ki values ≤0.5 μM.

In another embodiment, the compounds of the present invention have Factor XIa or plasma kallikrein Ki values ≤0.1 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate, thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s). In a preferred embodiment, the present invention provides pharmaceutical composition, wherein the additional therapeutic agent(s) are an anti-platelet agent or a combination thereof. Preferably, the anti-platelet agent(s) are clopidogrel and/or aspirin, or a combination thereof.

In another embodiment, the present invention provides a method for the treatment and/or prophylaxis of a thromboembolic disorder comprising administering to a patient in need of such treatment and/or prophylaxis a therapeutically effective amount of at least one of the compounds of the present invention or a stereoisomer, a tautomer, a pharmaceutically acceptable salt, or a solvate thereof.

In another embodiment, the present invention provides a compound of the present invention or a stereoisomer, a tautomer, a pharmaceutically acceptable salt, or a solvate thereof, for use in therapy.

In another embodiment, the present invention provides a compound of the present invention or a stereoisomer, a tautomer, a pharmaceutically acceptable salt, or a solvate thereof, for use in therapy for the treatment and/or prophylaxis of a thromboembolic disorder.

In another embodiment, the present invention also provides the use of a compound of the present invention or a stereoisomer, a tautomer, a pharmaceutically acceptable salt, or a solvate thereof, for the manufacture of a medicament for the treatment and/or prophylaxis of a thromboembolic disorder.

In another embodiment, the present invention provides a method for treatment and/or prophylaxis of a thromboembolic disorder, comprising: administering to a patient in need thereof a therapeutically effective amount of a first and second therapeutic agent, wherein the first therapeutic agent is a compound of the present invention or a stereoisomer, a tautomer, a pharmaceutically acceptable salt, or a solvate thereof, and the second therapeutic agent is at least one agent selected from a Factor Xa inhibitor such as apixaban, rivaroxaban, betrixaban, edoxaban, an anti-coagulant agent, an anti-platelet agent, a thrombin inhibiting agent such as dabigatran, a thrombolytic agent, and a fibrinolytic agent. Preferably, the second therapeutic agent is at least one agent selected from warfarin, unfractionated heparin, low molecular weight heparin, synthetic pentasaccharide, hirudin, argatroban, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, desulfatohirudin, tissue plasminogen activator, modified tissue plasminogen activator, anistreplase, urokinase, and streptokinase. Preferably, the second therapeutic agent is at least one anti-platelet agent. Preferably, the anti-platelet agent(s) are clopidogrel and/or aspirin, or a combination thereof.

The thromboembolic disorder includes arterial cardiovascular thromboembolic disorders, venous cardiovascular thromboembolic disorders, arterial cerebrovascular thromboembolic disorders, and venous cerebrovascular thromboembolic disorders. Examples of the thromboembolic disorder include, but are not limited to, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a method for the treatment and/or prophylaxis of an inflammatory disorder comprising: administering to a patient in need of such treatment and/or prophylaxis a therapeutically effective amount of at least one of the compounds of the present invention or a stereoisomer, a tautomer, a pharmaceutically acceptable salt, or a solvate thereof. Examples of the inflammatory disorder include, but are not limited to, sepsis, acute respiratory distress syndrome, and systemic inflammatory response syndrome.

In another embodiment, the present invention provides a method for the prophylaxis of a disease or condition in which plasma kallikrein activity is implicated comprising administering to a patient in need of such treatment and/or prophylaxis a therapeutically effective amount of at least one of the compounds of the present invention or a stereoisomer, a tautomer, a pharmaceutically acceptable salt, or a solvate thereof.

The disease or condition in which plasma kallikrein activity is implicated includes, but not limited to, impaired visual acuity, diabetic retinopathy, diabetic macular edema, hereditary angioedema, diabetes, pancreatitis, nephropathy, cardio myopathy, neuropathy, inflammatory bowel disease, arthritis, inflammation, septic shock, hypotension, cancer, adult respiratory distress syndrome, disseminated intravascular coagulation, and cardiopulmonary bypass surgery.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment and/or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example, methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example, trifluoromethyl-S—, and pentafluoroethyl-S—.

The term "alkoxyalkyl", as used herein, refers to an alkyl group substituted with one, two, or three alkoxy groups.

The term "amino", as used herein, refers to —$NH_2$.

The term "substituted amino", as used herein, refers to the defined terms below having the suffix "amino" such as "arylamino", "alkylamino", "arylamino", etc.

The term "alkoxyalkylamino", as used herein, refers to —NHR wherein R is an alkoxyalkyl group.

The term "alkoxycarbonyl", as used herein, refers to an alkoxy group attached to the parent molecular moiety through a carbonyl group.

The term "alkoxycarbonylamino", as used herein, refers to an —NHR wherein R is an alkoxycarbonyl group.

The term "alkylamino", as used herein refers to —NHR, wherein R is an alkyl group.

The term "alkylcarbonyl", as used herein, refers to an alkyl group attached to the parent molecular moiety through a carbonyl group.

The term "alkylcarbonylamino", as used herein, refers to —NHR wherein R is an alkylcarbonyl group.

The term "aminosulfonyl", as used herein, refers to —$SO_2NH_2$.

The term "arylalkyl", as used herein, refers to an alkyl group substituted with one, two, or three aryl groups.

The term "arylamino", as used herein, refers to —NHR wherein R is an aryl group.

The term "arylcarbonyl", as used herein, refers to an aryl group attached to the parent molecular moiety through a carbonyl group.

The term "arylcarbonylamino", as used herein refers to —NHR wherein R is an arylcarbonyl group.

The term "carbonyl", as used herein, refers to —C(O)—.

The term "cyano", as used herein, refers to —CN.

The term "cycloalkylamino", as used herein, refers to —NHR wherein R is a cycloalkyl group.

The term "cycloalkylcarbonyl", as used herein, refers to a cycloalkyl group attached to the parent molecular moiety through a carbonyl group.

The term "cycloalkylcarbonylamino", as used herein, refers to —NHR wherein R is a cycloalkylcarbonyl group.

The term "cycloalkyloxy", as used herein, refers to a cycloalkyl group attached to the parent molecular moiety through an oxygen atom.

The term "dialkylamino", as used herein, refers to $NR_2$, wherein each R is an alkyl group. The two alkyl groups are the same or different.

The term "haloalkoxy", as used herein, refers to a haloalkyl group attached to the parent molecular moiety through an oxygen atom.

The term "haloalkyl", as used herein, refers to an alkyl group substituted by one, two, three, or four halogen atoms.

The term "haloalkylamino", as used herein, refers to —NHR wherein R is a haloalkyl group.

The term "carbonyl" refers to C(=O).

The term "carboxy" refers to C(=O)OH.

The term "haloalkylcarbonyl", as used herein, refers to a haloalkyl group attached to the parent molecular moiety through a carbonyl group.

The term "haloalkylcarbonylamino", as used herein, refers to —NHR wherein R is a haloalkylcarbonyl group.

The terms "alkylcarbonyl" refer to an alkyl or substituted alkyl bonded to a carbonyl.

The term "alkoxycarbonyl", as used herein, refers to an alkoxy group attached to the parent molecular moiety through a carbonyl group.

The term "hydroxy" or "hydroxyl" refers to OH.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle" or "heterocyclic ring" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines, and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric, and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", A *Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988); and e) Kakeya, N. et al., *Chem. Pharm. Bull.*, 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes.

Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example, when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "RBF" for round bottom flask, "atm" for atmosphere, "psi" for pounds per square inch, "conc." for concentrate, "RCM" for ring-closing metathesis, "sat" or "sat'd" for saturated, "SFC" for supercritical fluid chromatography, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

| | |
|---|---|
| Me | methyl |
| Et | ethyl |
| Pr | propyl |
| i-Pr | isopropyl |
| Bu | butyl |
| i-Bu | isobutyl |
| t-Bu | tert-butyl |
| Ph | phenyl |
| Bn | benzyl |
| Boc | tert-butyloxycarbonyl |
| $Boc_2O$ | di-tert-butyl dicarbonate |
| AcOH or HOAc | acetic acid |
| $AlCl_3$ | aluminum chloride |
| AIBN | Azobisisobutyronitrile |
| $BBr_3$ | boron tribromide |
| $BCl_3$ | boron trichloride |
| BEMP | 2-tert-butylimino-2-diethylamino-1,3-dimethylperhydro-1,3,2-diazaphosphorine |
| BOP reagent | benzotriazol-1-yloxytris(dimethylamino)phosphonium hexafluorophosphate |
| Burgess reagent | 1-methoxy-N-triethylammoniosulfonyl-methanimidate |
| CBz | carbobenzyloxy |
| DCM or $CH_2Cl_2$ | dichloromethane |
| $CH_3CN$ or ACN | acetonitrile |
| $CDCl_3$ | deutero-chloroform |
| $CHCl_3$ | chloroform |
| mCPBA or m-CPBA | meta-chloroperbenzoic acid |
| $Cs_2CO_3$ | cesium carbonate |
| $Cu(OAc)_2$ | copper (II) acetate |
| $Cy_2NMe$ | N-cyclohexyl-N-methylcyclohexanamine |
| DBU | 1,8-diazabicyclo[5.4.0]undec-7-ene |
| DCE | 1,2 dichloroethane |
| DEA | diethylamine |
| Dess-Martin | 1,1,1-tris(acetyloxy)-1,1-dihydro-1,2-beniziodoxol-3-(1H)-one |
| DIC or DIPCDI | diisopropylcarbodiimide |
| DIEA, DIPEA or Hunig's base | diisopropylethylamine |
| DMAP | 4-dimethylaminopyridine |
| DME | 1,2-dimethoxyethane |
| DMF | dimethyl formamide |
| DMSO | dimethyl sulfoxide |
| cDNA | complimentary DNA |
| Dppp | (R)-(+)-1,2-bis(diphenylphosphino)propane |
| DuPhos | (+)-1,2-bis((2S,5S)-2,5-diethylpholano)benzene |
| EDC | N-(3-dimthylaminopropyl)-N'-ethylcarbodiimide |

| | -continued |
|---|---|
| EDCI | N-(3-dimthylaminopropyl)-N'-ethylcarbodiimide hydrochloride |
| EDTA | ethylenediaminetetraacetic acid |
| (S,S)-EtDuPhosRh(I) | (+)-1,2-bis((2S,5S)-2,5-diethylphospholano)benzene (1,5-cyclooctadiene)rhodium(I) trifluoromethanesulfonate |
| $Et_3N$ or TEA | triethylamine |
| EtOAc | ethyl acetate |
| $Et_2O$ | diethyl ether |
| EtOH | ethanol |
| GMF | glass microfiber filter |
| Grubbs II | (1,3-bis(2,4,6-trimethylphenyl)-2-imidazolidinylidene) dichloro(phenylmethylene) (triycyclohexylphosphine)ruthenium |
| HCl | hydrochloric acid |
| HATU | O-(7-azabenzotriazol-1-yl)-N,N,N',N'-tetramethyluronium hexafluorophosphate |
| HEPES | 4-(2-hydroxyethyl)piperaxine-1-ethanesulfonic acid |
| Hex | hexane |
| HOBt or HOBT | 1-hydroxybenzotriazole |
| IBX | 2-iodoxybenzoic acid |
| $H_2SO_4$ | sulfuric acid |
| Jones reagent | $CrO_3$ in aqueous $H_2SO_4$, 2M |
| $K_2CO_3$ | potassium carbonate |
| $K_2HPO_4$ | potassium phosphate dibasic |
| KOAc | potassium acetate |
| $K_3PO_4$ | potassium phosphate |
| LAH | lithium aluminum hydride |
| LG | leaving group |
| LiOH | lithium hydroxide |
| MeOH | methanol |
| $MgSO_4$ | magnesium sulfate |
| MsOH or MSA | methylsulfonic acid |
| NaCl | sodium chloride |
| NaH | sodium hydride |
| $NaHCO_3$ | sodium bicarbonate |
| $Na_2CO_3$ | sodium carbonate |
| NaOH | sodium hydroxide |
| $Na_2SO_3$ | sodium sulfite |
| $Na_2SO_4$ | sodium sulfate |
| NBS | N-bromosuccinimide |
| NCS | N-chlorosuccinimide |
| $NH_3$ | ammonia |
| $NH_4Cl$ | ammonium chloride |
| $NH_4OH$ | ammonium hydroxide |
| $NH_4COOH$ | ammonium formate |
| OTf | triflate or trifluoromethanesulfonate |
| $Pd_2(dba)_3$ | tris(dibenzylideneacetone)dipalladium(0) |
| $Pd(OAc)_2$ | palladium(II) acetate |
| Pd/C | palladium on carbon |
| $Pd(dppf)Cl_2$ | [1,1'-bis(diphenylphosphino)-ferrocene] dichloropalladium(II) |
| $Ph_3PCl_2$ | triphenylphosphine dichloride |
| PG | protecting group |
| $POCl_3$ | phosphorus oxychloride |
| i-PrOH or IPA | isopropanol |
| PS | Polystyrene |
| SEM-Cl | 2-(trimethysilyl)ethoxymethyl chloride |
| $SiO_2$ | silica oxide |
| $SnCl_2$ | tin(II) chloride |
| TBAI | tetra-n-butylammonium iodide |
| TFA | trifluoroacetic acid |
| THF | tetrahydrofuran |
| $TMSCHN_2$ | trimethylsilyldiazomethane |
| T3P ® | propane phosphonic acid anhydride |
| TRIS | tris (hydroxymethyl) aminomethane |
| pTsOH | p-toluenesulfonic acid |

The compounds of the present invention can be prepared in a number of ways known to one skilled in the art of organic synthesis.

IV. Biology

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thromboembolic disorders and include acute coronary syndrome, unstable angina, myocardial infarction, thrombosis in the cavity of the heart, ischemic stroke, deep vein thrombosis, peripheral occlusive arterial disease, transient ischemic attack, and pulmonary embolism. In addition, thrombosis occurs on artificial surfaces in contact with blood, including catheters, stents, artificial heart valves, and hemodialysis membranes.

Some conditions contribute to the risk of developing thrombosis. For example, alterations of the vessel wall, changes in the flow of blood, and alterations in the composition of the vascular compartment. These risk factors are collectively known as Virchow's triad. (Colman, R. W. et al., eds., *Hemostasis and Thrombosis, Basic Principles and Clinical Practice*, Fifth Edition, p. 853, Lippincott Williams & Wilkins (2006)).

Antithrombotic agents are frequently given to patients at risk of developing thromboembolic disease because of the presence of one or more predisposing risk factors from Virchow's triad to prevent formation of an occlusive thrombus (primary prevention). For example, in an orthopedic surgery setting (e.g., hip and knee replacement), an antithrombotic agent is frequently administered prior to a surgical procedure. The antithrombotic agent counterbalances the prothrombotic stimulus exerted by vascular flow alterations (stasis), potential surgical vessel wall injury, as well as changes in the composition of the blood due to the acute phase response related to surgery. Another example of the use of an antithrombotic agent for primary prevention is dosing with aspirin, a platelet activation inhibitor, in patients at risk for developing thrombotic cardiovascular disease. Well recognized risk factors in this setting include age, male gender, hypertension, diabetes mellitus, lipid alterations, and obesity.

Antithrombotic agents are also indicated for secondary prevention, following an initial thrombotic episode. For example, patients with mutations in Factor V (also known as Factor V Leiden) and additional risk factors (e.g., pregnancy), are dosed with anticoagulants to prevent the reoccurrence of venous thrombosis. Another example entails secondary prevention of cardiovascular events in patients with a history of acute myocardial infarction or acute coronary syndrome. In a clinical setting, a combination of aspirin and clopidogrel (or other thienopyridines) may be used to prevent a second thrombotic event.

Antithrombotic agents are also given to treat the disease state (i.e., by arresting its development) after it has already started. For example, patients presenting with deep vein thrombosis are treated with anticoagulants (i.e., heparin, warfarin, or LMWH) to prevent further growth of the venous occlusion. Over time, these agents also cause a regression of the disease state because the balance between prothrombotic factors and anticoagulant/profibrinolytic pathways is changed in favor of the latter. Examples on the arterial vascular bed include the treatment of patients with acute myocardial infarction or acute coronary syndrome with aspirin and clopidogrel to prevent further growth of vascular occlusions and eventually leading to a regression of thrombotic occlusions.

Thus, antithrombotic agents are used widely for primary and secondary prevention (i.e., prophylaxis or risk reduction) of thromboembolic disorders, as well as treatment of an already existing thrombotic process. Drugs that inhibit blood coagulation, or anticoagulants, are "pivotal agents for prevention and treatment of thromboembolic disorders" (Hirsh, J. et al., *Blood*, 105:453-463 (2005)).

An alternative way of initiation of coagulation is operative when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of Factor XII leads to a conformational change in the Factor XII molecule, thereby facilitating activation to proteolytic active Factor XII molecules (Factor XIIa and Factor XIIf). Factor XIIa (or XIIf) has a number of target proteins, including plasma prekallikrein and Factor XI. Active plasma kallikrein further activates Factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., *Blood*, 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact Activation Pathway", *Hemostasis and Thrombosis*, pp. 103-122, Lippincott Williams & Wilkins (2001); Schmaier, A. H., "Contact Activation", *Thrombosis and Hemorrhage*, pp. 105-128 (1998)). The biological relevance of the contact activation system for thromboembolic diseases is supported by the phenotype of Factor XII deficient mice. More specifically, Factor XII deficient mice were protected from thrombotic vascular occlusion in several thrombosis models as well as stroke models and the phenotype of the XII deficient mice was identical to XI deficient mice (Renne et al., *J. Exp. Med.*, 202:271-281 (2005); Kleinschmitz et al., *J. Exp. Med.*, 203:513-518 (2006)). The fact that Factor XI is down-stream from Factor XIIa, combined with the identical phenotype of the XII and XI deficient mice suggest that the contact activation system could play a major role in Factor XI activation in vivo.

Factor XI is a zymogen of a trypsin-like serine protease and is present in plasma at a relatively low concentration. Proteolytic activation at an internal R369-I370 bond yields a heavy chain (369 amino acids) and a light chain (238 amino acids). The latter contains a typical trypsin-like catalytic triad (H413, D464, and S557). Activation of Factor XI by thrombin is believed to occur on negatively charged surfaces, most likely on the surface of activated platelets. Platelets contain high affinity (0.8 nM) specific sites (130-500/platelet) for activated Factor XI. After activation, Factor XIa remains surface bound and recognizes Factor IX as its normal macromolecular substrate. (Galiani, D., Trends Cardiovasc. Med., 10:198-204 (2000)).

In addition to the feedback activation mechanisms described above, thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al., *Thromb. Res.*, 101:329-354 (2001).) Thus, inhibitors of Factor XIa are expected to be anticoagulant and profibrinolytic.

Further evidence for the anti-thromboembolic effects of targeting Factor XI is derived from mice deficient in Factor XI. It has been demonstrated that complete fXI deficiency protected mice from ferric chloride ($FeCl_3$)-induced carotid artery thrombosis (Rosen et al., *Thromb. Haemost.*, 87:774-777 (2002); Wang et al., *J. Thromb. Haemost.*, 3:695-702 (2005)). Also, Factor XI deficiency rescues the perinatal lethal phenotype of complete protein C deficiency (Chan et al., *Amer. J. Pathol.*, 158:469-479 (2001)). Furthermore, baboon cross-reactive, function blocking antibodies to human Factor XI protect against baboon arterial—venous shunt thrombosis (Gruber et al., *Blood*, 102:953-955 (2003)). Evidence for an antithrombotic effect of small molecule inhibitors of Factor XIa is also disclosed in published U.S. Publication No. 2004/0180855 A1. Taken together, these studies suggest that targeting Factor XI will reduce the propensity for thrombotic and thromboembolic diseases.

Genetic evidence indicates that Factor XI is not required for normal homeostasis, implying a superior safety profile of the Factor XI mechanism compared to competing antithrombotic mechanisms. In contrast to hemophilia A (Factor VIII deficiency) or hemophilia B (Factor IX deficiency), mutations of the Factor XI gene causing Factor XI deficiency (hemophilia C) result in only a mild to moderate bleeding diathesis characterized primarily by postoperative or posttraumatic, but rarely spontaneous hemorrhage. Postoperative bleeding occurs mostly in tissue with high concentrations of endogenous fibrinolytic activity (e.g., oral cavity, and urogenital system). The majority of the cases are fortuitously identified by preoperative prolongation of aPTT (intrinsic system) without any prior bleeding history.

The increased safety of inhibition of XIa as an anticoagulation therapy is further supported by the fact that Factor XI knock-out mice, which have no detectable Factor XI protein, undergo normal development, and have a normal life span. No evidence for spontaneous bleeding has been noted. The aPTT (intrinsic system) is prolonged in a gene dose-dependent fashion. Interestingly, even after severe stimulation of the coagulation system (tail transection), the bleeding time is not significantly prolonged compared to wild-type and heterozygous litter mates. (Gailani, D., *Frontiers in Bioscience*, 6:201-207 (2001); Gailani, D. et al., *Blood Coagulation and Fibrinolysis*, 8:134-144 (1997).) Taken together, these observations suggest that high levels of inhibition of Factor XIa should be well tolerated. This is in contrast to gene targeting experiments with other coagulation factors, excluding Factor XII.

In vivo activation of Factor XI can be determined by complex formation with either C1 inhibitor or alpha 1 antitrypsin. In a study of 50 patients with acute myocardial infarction (AMI), approximately 25% of the patients had values above the upper normal range of the complex ELISA. This study can be viewed as evidence that at least in a subpopulation of patients with AMI, Factor XI activation contributes to thrombin formation (Minnema, M. C. et al., *Arterioscler. Thromb. Vasc. Biol.*, 20:2489-2493 (2000)). A second study establishes a positive correlation between the extent of coronary arteriosclerosis and Factor XIa in complex with alpha 1 antitrypsin (Murakami, T. et al., *Arterioscler. Thromb. Vasc. Biol.*, 15:1107-1113 (1995)). In another study, Factor XI levels above the 90th percentile in patients were associated with a 2.2-fold increased risk for venous thrombosis (Meijers, J. C. M. et al., *N. Engl. J. Med.*, 342:696-701 (2000)).

Also, it is preferred to find new compounds with improved activity in in vitro clotting assays, compared with known serine protease inhibitors, such as the activated partial thromboplastin time (aPTT) or prothrombin time (PT) assay. (for a description of the aPTT and PT assays see, Goodnight, S. H. et al., "Screening Tests of Hemostasis", *Disorders of Thrombosis and Hemostasis: A Clinical Guide*, Second Edition, pp. 41-51, McGraw-Hill, New York (2001)).

It is also desirable and preferable to find compounds with advantageous and improved characteristics compared with known serine protease inhibitors, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) factors that improve manufacturing costs or feasibility.

Pre-clinical studies demonstrated significant antithrombotic effects of small molecule Factor XIa inhibitors in rabbit and rat model of arterial thrombosis, at doses that preserved hemostasis. (Wong P. C. et al., *American Heart Association Scientific Sessions*, Abstract No. 6118, Nov. 12-15, 2006; Schumacher, W. et al., *J. Thromb. Haemost.*, 3(Suppl. 1):P1228 (2005); Schumacher, W. A. et al., *Eur. J. Pharmacol.*, 167-174 (2007)). Furthermore, it was observed that in vitro prolongation of the aPTT by specific XIa inhibitors is a good predictor of efficacy in our thrombosis models. Thus, the in vitro aPTT test can be used as a surrogate for efficacy in vivo.

As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit Factor XIa and/or plasma kallikrein and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi); clotting within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to are family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Risk factors for congenital thrombophilia include gain of function mutations in coagulation factors or loss of function mutations in the anticoagulant- or fibrinolytic pathways.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population (Levitan, N. et al., *Medicine* (Baltimore), 78(5):285-291 (1999); Levine M. et al., *N. Engl. J. Med.*, 334(11):677-681 (1996); Blom, J. W. et al., *JAMA*, 293(6):715-722 (2005)). Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and anti-angiogenic drugs. Thus, it is common clinical practice to dose patients having advanced tumors with heparin or low molecular heparin to prevent thromboembolic disorders. A number of low molecular heparin preparations have been approved by the FDA for these indications.

There are three main clinical situations when considering the prevention of VTE in a medical cancer patient: (i) the patient is bedridden for prolonged periods of time; (ii) the ambulatory patient is receiving chemotherapy or radiation; and (iii) the patient is with indwelling central vein catheters. Unfractionated heparin (UFH) and low molecular weight heparin (LMWH) are effective antithrombotic agents in cancer patients undergoing surgery. (Mismetti, P. et al., *Brit. J. Surg.*, 88:913-930 (2001).)

A. In Vitro Assays

The effectiveness of compounds of the present invention as inhibitors of the coagulation Factors XIa, VIIa, IXa, Xa, XIIa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin), which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 25-200 pM (Haematologic Technologies) and the synthetic substrate S-2366 (pyroGlu-Pro-Arg-pNA; CHROMOGENIX® or AnaSpec) at a concentration of 0.0002-0.001 M.

Factor VIIa determinations were made in 0.005 M calcium chloride, 0.15 M sodium chloride, 0.05 M HEPES buffer containing 0.1% PEG 8000 at a pH of 7.5. Determinations were made using purified human Factor VIIa (Haematologic Technologies) or recombinant human Factor VIIa (Novo Nordisk) at a final assay concentration of 0.5-10 nM, recombinant soluble tissue factor at a concentration of 10-40 nM and the synthetic substrate H-D-Ile-Pro-Arg-pNA (S-2288; CHROMOGENIX® or BMPM-2; AnaSpec) at a concentration of 0.001-0.0075 M.

Factor IXa determinations were made in 0.005 M calcium chloride, 0.1 M sodium chloride, 0.0000001 M Refludan (Berlex), 0.05 M TRIS base and 0.5% PEG 8000 at a pH of 7.4. Refludan was added to inhibit small amounts of thrombin in the commercial preparations of human Factor IXa. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Ph'Gly-Arg-AMC; CenterChem) at a concentration of 0.0004-0.0005 M.

Factor Xa determinations were made in 0.1 M sodium phosphate buffer at a pH of 7.5 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA; CHROMOGENIX®) at a concentration of 0.0002-0.00035 M.

Factor XIIa determinations were made in 0.05 M HEPES buffer at pH 7.4 containing 0.145 M NaCl, 0.05 M KCl, and 0.1% PEG 8000. Determinations were made using purified human Factor XIIa at a final concentration of 4 nM (American Diagnostica) and the synthetic substrate SPECTROZYME® #312 (H-D-CHT-Gly-L-Arg-pNA.2AcOH; American Diagnostica) at a concentration of 0.00015 M.

Plasma kallikrein determinations were made in 0.1 M sodium phosphate buffer at a pH of 7.5 containing 0.1-0.2 M sodium chloride and 0.5% PEG 8000. Determinations were made using purified human plasma kallikrein (Enzyme Research Laboratories) at a final assay concentration of 200 pM and the synthetic substrate S-2302 (H-(D)-Pro-Phe-Arg-pNA; CHROMOGENIX®) at a concentration of 0.00008-0.0004 M.

Thrombin determinations were made in 0.1 M sodium phosphate buffer at a pH of 7.5 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; CHROMOGENIX® or AnaSpec) at a concentration of 0.0002-0.0004 M.

The Michaelis constant, $K_m$, for substrate hydrolysis by each protease, was determined at 25° C. or 37° C. in the absence of inhibitor. Values of $K_i$ were determined by allowing the protease to react with the substrate in the presence of the inhibitor. Reactions were allowed to go for periods of 20-180 minutes (depending on the protease) and the velocities (rate of absorbance or fluorescence change versus time) were measured. The following relationships were used to calculate $K_i$ values:

$(V_{max}*S)/(K_m+S)$;

$(v_o-v_s)/v_s = I/(K_i(1+S/K_m))$ for a competitive inhibitor with one binding site; or $v_s/v_o = A + (B-A)/(1+(I/IC_{50})^n)$; and $K_i = IC_{50}/(1+S/K_m)$ for a competitive inhibitor where:
$v_o$ is the velocity of the control in the absence of inhibitor;
$v_s$ is the velocity in the presence of inhibitor;
$V_{max}$ is the maximum reaction velocity;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;

$IC_{50}$ is the concentration of inhibitor that produces 50% inhibition under the assay conditions;
$K_i$ is the dissociation constant of the enzyme: inhibitor complex;
S is the concentration of substrate; and
$K_m$ is the Michaelis constant for the substrate.

The selectivity of a compound may be evaluated by taking the ratio of the $K_i$ value for a given protease with the $K_i$ value for the protease of interest (i.e., selectivity for FXIa versus protease P=$K_i$ for protease P/$K_i$ for FXIa). Compounds with selectivity ratios >20 are considered selective.

The effectiveness of compounds of the present invention as inhibitors of coagulation can be determined using a standard or modified clotting assay. An increase in the plasma clotting time in the presence of inhibitor is indicative of anticoagulation. Relative clotting time is the clotting time in the presence of an inhibitor divided by the clotting time in the absence of an inhibitor. The results of this assay may be expressed as IC1.5× or IC2×, the inhibitor concentration required to increase the clotting time by 50 or 100 percent, respectively. The IC1.5× or IC2× is found by linear interpolation from relative clotting time versus inhibitor concentration plots using inhibitor concentration that spans the IC1.5× or IC2×.

Clotting times are determined using citrated normal human plasma as well as plasma obtained from a number of laboratory animal species (e.g., rat, or rabbit). A compound is diluted into plasma beginning with a 10 mM DMSO stock solution. The final concentration of DMSO is less than 2%. Plasma clotting assays are performed in an automated coagulation analyzer (SYSMEX®, Dade-Behring, Illinois). Similarly, clotting times can be determined from laboratory animal species or humans dosed with compounds of the invention.

Activated Partial Thromboplastin Time (aPTT) is determined using ACTIN® FSL (Dade-Behring, Illinois) following the directions in the package insert. Plasma (0.05 mL) is warmed to 37° C. for 1 minute. ACTIN® FSL (0.05 mL) is added to the plasma and incubated for an additional 2 to 5 minutes. Calcium chloride (25 mM, 0.05 mL) is added to the reaction to initiate coagulation. The clotting time is the time in seconds from the moment calcium chloride is added until a clot is detected.

Prothrombin Time (PT) is determined using thromboplastin (Thromboplastin C Plus or INNOVIN®, Dade-Behring, Illinois) following the directions in the package insert. Plasma (0.05 mL) is warmed to 37° C. for 1 minute. Thromboplastin (0.1 mL) is added to the plasma to initiate coagulation. The clotting time is the time in seconds from the moment thromboplastin is added until a clot is detected.

The exemplified Examples disclosed below were tested in the Factor XIa assay described above and found having Factor XIa inhibitory activity. A range of Factor XIa inhibitory activity (Ki values) of 10≤µM (10000 nM) was observed. Table 1 below lists Factor XIa Ki values measured at 37° C. for the following Examples.

TABLE 1

| Example No. | Factor XIa Ki (nM) |
|---|---|
| 1 | 17.89 |
| 2 | 2177.00 |
| 3 | 41.87 |
| 4 | 1495.00 |
| 5 | 825.00 |
| 6 | 627.40 |
| 7 | 708.00 |

TABLE 1-continued

| Example No. | Factor XIa Ki (nM) |
| --- | --- |
| 8 | 1337.00 |
| 9 | 2065.00 |
| 10 | 2621.00 |
| 11 | 73.61 |
| 12 | 81.83 |
| 13 | 34.33 |
| 14 | 336.30 |
| 15 | 812.00 |
| 16 | 73.25 |
| 17 | 104.20 |
| 18 | 54.32 |
| 19 | 595.90 |
| 20 | 9293.00 |
| 21 | 14.09 |
| 22 | <5.00 |
| 23 | 156.90 |
| 24 | 153.30 |
| 25 | <5.00 |
| 26 | 64.08 |
| 27 | 39.08 |
| 28 | 338.00 |
| 29 | 1405.00 |
| 30 | 2197.00 |
| 31 | 811.20 |
| 32 | 17.43 |
| 33 | 6.24 |
| 34 | <5.00 |
| 35 | 216.30 |

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient. In one embodiment, the pharmaceutical composition is a solid formulation, e.g., a spray-dried composition, which may be used as is, or whereto the physician or the patient adds solvents, and/or diluents prior to use.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels. Solid dispersions are also called solid-state dispersions. In some embodiments, any compound described herein is formulated as a spray dried dispersion (SDD). An SDD is a single phase amorphous molecular dispersion of a drug in a polymer matrix. It is a solid solution prepared by dissolving the drug and a polymer in a solvent (e.g., acetone, methanol or the like) and spray drying the solution. The solvent rapidly evaporates from droplets which rapidly solidifies the polymer and drug mixture trapping the drug in amorphous form as an amorphous molecular dispersion.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like.

Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to about 100 milligrams of the compound of the present invention and about 0.1 to about 100 milligrams per kilogram of patient body weight. For a tablet dosage form, the compounds of this invention generally may be present in an amount of about 5 to about 300 milligrams per dosage unit, and the second anti-coagulant in an amount of about 1 to about 500 milligrams per dosage unit.

Where the compounds of the present invention are administered in combination with an anti-platelet agent, by way of general guidance, typically a daily dosage may be about 0.01 to about 300 milligrams of the compound of the present invention and about 50 to about 150 milligrams of the anti-platelet agent, preferably about 0.1 to about 4 milligrams of the compound of the present invention and about 1 to about 3 milligrams of antiplatelet agents, per kilogram of patient body weight.

Where the compounds of the present invention are administered in combination with thrombolytic agent, typically a daily dosage may be about 0.1 to about 100 milligrams of the compound of the present invention, per kilogram of patient body weight and, in the case of the thrombolytic agents, the usual dosage of the thrombolytic agent when administered alone may be reduced by about 50-80% when administered with a compound of the present invention.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In another embodiment, the present invention provides a pharmaceutical composition further comprising additional therapeutic agent(s) selected from potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an antiarrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In another embodiment, the present invention provides a pharmaceutical composition wherein the additional therapeutic agent is an antihypertensive agent selected from ACE inhibitors, AT-1 receptor antagonists, beta-adrenergic receptor antagonists, ETA receptor antagonists, dual ETA/AT-1 receptor antagonists, renin inhibitors (aliskiren) and vasopepsidase inhibitors, an antiarrythmic agent selected from $I_{Kur}$ inhibitors, an anticoagulant selected from thrombin inhibitors, antithrombin-III activators, heparin co-Factor II activators, other Factor XIa inhibitors, other kallikrein inhibitors, plasminogen activator inhibitor (PAI-1) antagonists, thrombin activatable fibrinolysis inhibitor (TAFI) inhibitors, Factor VIIa inhibitors, Factor IXa inhibitors, and Factor Xa inhibitors, or an antiplatelet agent selected from GPIIb/IIIa blockers, GP Ib/IX blockers, protease activated receptor 1 (PAR-1) antagonists, protease activated receptor4 (PAR-4) antagonists, prostaglandin E2 receptor EP3 antagonists, collagen receptor antagonists, phosphodiesterase-III inhibitors, $P2Y_1$ receptor antagonists, $P2Y_{12}$ antagonists, thromboxane receptor antagonists, cyclooxygense-1 inhibitors, and aspirin, or a combination thereof.

In another embodiment, the present invention provides pharmaceutical composition, wherein the additional therapeutic agent(s) are an anti-platelet agent or a combination thereof.

In another embodiment, the present invention provides a pharmaceutical composition, wherein the additional therapeutic agent is the anti-platelet agent clopidogrel.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

Compounds that can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example, LOVENOX®), synthetic pentasaccharide, direct acting thrombin inhibitors including hirudin and argatroban, as well as other Factor VIIa inhibitors, Factor IXa inhibitors, Factor Xa inhibitors (e.g., ARIXTRA®, apixaban, rivaroxaban, LY-517717, DU-176b, DX-9065a, and those disclosed in WO 98/57951, WO 03/026652, WO 01/047919, and WO 00/076970), Factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granule-content secretion of platelets. Such agents include, but are not limited to, the various known non-steroidal anti-inflammatory drugs (NSAIDs) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDs, aspirin (acetylsalicylic acid or ASA) and piroxicam are preferred. Other suitable platelet inhibitory agents include glycoprotein IIb/IIIa antagonists (e.g., tirofiban, eptifibatide, abciximab, and integrelin), thromboxane-A2-receptor antagonists (e.g., ifetroban), thromboxane-A-synthetase inhibitors, phosphodiesterase-III (PDE-III) inhibitors (e.g., dipyridamole, cilostazol), and PDE-V inhibitors (such as sildenafil), protease-activated receptor 1 (PAR-1) antagonists (e.g., E-5555, SCH-530348, SCH-203099, SCH-529153 and SCH-205831), and pharmaceutically acceptable salts or prodrugs thereof.

Other examples of suitable anti-platelet agents for use in combination with the compounds of the present invention, with or without aspirin, are ADP (adenosine diphosphate) receptor antagonists, preferably antagonists of the purinergic receptors $P2Y_1$ and $P2Y_{12}$, with $P2Y_{12}$ being even more preferred. Preferred $P2Y_{12}$ receptor antagonists include clopidogrel, ticlopidine, prasugrel, ticagrelor, and cangrelor, and pharmaceutically acceptable salts or prodrugs thereof. Ticlopidine and clopidogrel are also preferred compounds since they are known to be more gentle than aspirin on the gastro-intestinal tract in use. Clopidogrel is an even more preferred agent.

A preferred example is a triple combination of a compound of the present invention, aspirin, and another anti-platelet agent. Preferably, the anti-platelet agent is clopidogrel or prasugrel, more preferably clopidogrel.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), Factor VIIa inhibitors, thrombin inhibitors, inhibitors of Factors IXa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable cholesterol/lipid lowering agents and lipid profile therapies for use in combination with the compounds of the present invention include HMG-CoA reductase inhibitors (e.g., pravastatin, lovastatin, simvastatin, fluvastatin, atorvastatin, rosuvastatin, and other statins), low-density lipoprotein (LDL) receptor activity modulators (e.g., HOE-402, PCSK9 inhibitors), bile acid sequestrants (e.g., cholestyramine and colestipol), nicotinic acid or derivatives thereof (e.g., NIASPAN®), GPR109B (nicotinic acid receptor) modulators, fenofibric acid derivatives (e.g., gemfibrozil, clofibrate, fenofibrate and benzafibrate) and other peroxisome proliferator-activated receptors (PPAR) alpha modulators, PPARdelta modulators (e.g., GW-501516), PPARgamma modulators (e.g., rosiglitazone), compounds that have multiple functionality for modulating the activities of various combinations of PPARalpha, PPARgamma and PPARdelta, probucol or derivatives thereof (e.g., AGI-1067), cholesterol absorption inhibitors and/or Niemann-Pick C1-like transporter inhibitors (e.g., ezetimibe), cholesterol ester transfer protein inhibitors (e.g., CP-529414), squalene synthase inhibitors and/or squalene epoxidase inhibitors or mixtures thereof, acyl coenzyme A: cholesteryl acyltransferase (ACAT) 1 inhibitors, ACAT2 inhibitors, dual ACAT1/2 inhibitors, ileal bile acid transport inhibitors (or apical sodium co-dependent bile acid transport inhibitors), microsomal triglyceride transfer protein inhibitors, liver-X-receptor (LXR) alpha modulators, LXRbeta modulators, LXR dual alpha/beta modulators, FXR modulators, omega 3 fatty acids (e.g., 3-PUFA), plant stanols and/or fatty acid esters of plant stanols (e.g., sitostanol ester used in BENECOL® margarine), endothelial lipase inhibitors, and HDL functional mimetics which activate reverse cholesterol transport (e.g., apoAI derivatives or apoAI peptide mimetics).

The compounds of the present invention are also useful as standard or reference compounds, for example, as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example, S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 µM against the target protease and greater than or equal to 0.1 µM against the other proteases, may also be used in diagnostic assays involving the quantitation of thrombin, Factor VIIa, IXa, Xa, XIa, and/or plasma kallikrein in serum samples. For example, the amount of Factor XIa in serum samples could be determined by careful titration of protease activity in the presence of the relevant chromogenic substrate, S2366, with a potent Factor XIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Example compounds are typically prepared as racemic mixtures. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Fourth Edition, Wiley-Interscience (2006)).

Representative compounds of this invention can be derived from intermediates 1g, the synthesis of which is described in Scheme 1. Esterification of amino acid 1a gives amino ester 1b. Amino ester 1b can then be coupled with an appropriately substituted carboxylic acid 1h using coupling agent, such as EDC/HOBt. Aniline 1c can then be coupled with an appropriately substituted carboxylic acid 1j using T3P® and a base, such as pyridine, to give the amide 1d. Using a modified procedure described by Lovely (*Tetrahedron Lett.*, 44:1379 (2003)), 1d can be cyclized via ring-closing metathesis using a catalyst, such as Grubbs (II), in a suitable solvent, such as DCM, DCE, or toluene at elevated temperature, to give the macrocycle 1e. The alkene can be reduced with hydrogen over either palladium on carbon or platinum oxide to provide ester 1f. Hydrolysis of ester 1f gives acid 1g. Compounds of the formula (I) can be synthesized from the coupling reaction of acid 1g and amine 1i by using coupling agents, such as HATU.

Scheme 1
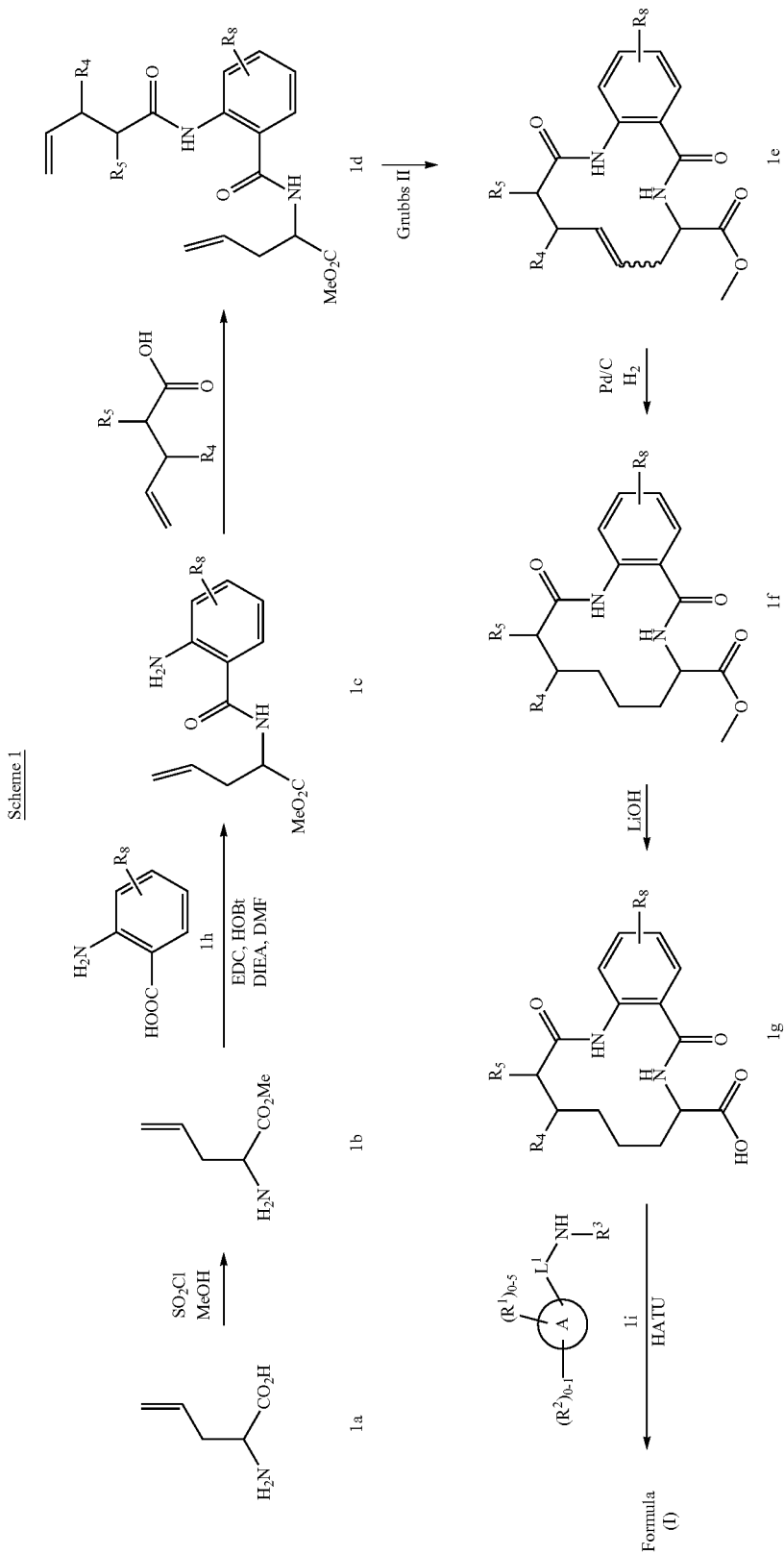

Olefin containing macrocycles of this invention can also be prepared according to Scheme 2. Hydrolysis of ester 1e gives acid 2a. Compounds of the formula (I) can be synthesized from the coupling reaction of acid 2a and amine 1i by using coupling agents, such as HATU.

Scheme 2

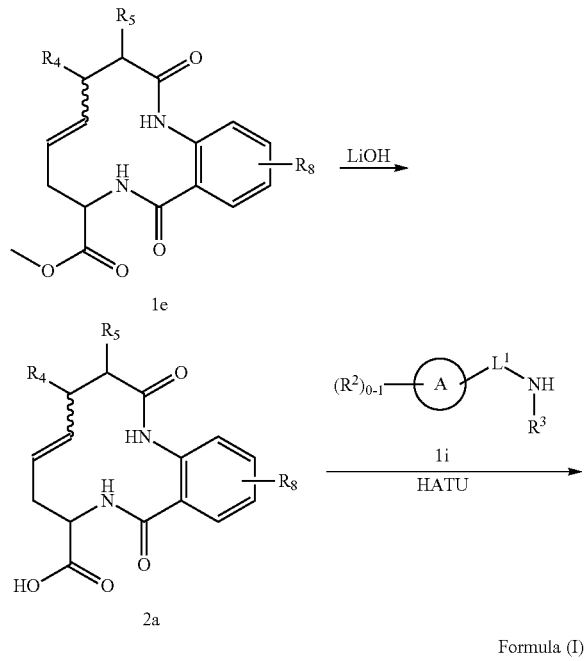

Formula (I)

Purification of intermediates and final products was carried out via either normal or reverse phase chromatography. Normal phase chromatography was carried out using prepacked $SiO_2$ cartridges eluting with either gradients of hexanes and ethyl acetate or DCM and MeOH unless otherwise indicated. Reverse phase preparative HPLC was carried out using C18 columns eluting with gradients of Solvent A (90% water, 10% MeOH, 0.1% TFA) and Solvent B (10% water, 90% MeOH, 0.1% TFA, UV 220 nm) or with gradients of Solvent A (90% water, 10% ACN, 0.1% TFA) and Solvent B (10% water, 90% ACN, 0.1% TFA, UV 220 nm) or with gradients of Solvent A (98% water, 2% ACN, 0.05% TFA) and Solvent B (98% ACN, 2% water, 0.05% TFA, UV 220 nm) (or) SunFire Prep C18 OBD 5µ 30×100 mm, 25 min gradient from 0-100% B. A=$H_2O$/ACN/TFA 90:10:0.1. B=ACN/$H_2O$/TFA 90:10:0.1

Unless otherwise stated, analysis of final products was carried out by reverse phase analytical HPLC.

Method A: A majority of analytical HPLC runs were: SunFire (4.6×150 mm) (15 min gradient—95:5 $H_2O$/ACN— to 95:5 ACN/$H_2O$-0.05% TFA).

Method B: A minority of analytical HPLC runs were: ZORBAX® (4.6×75 mm) (8 min gradient—10:90 MeOH/$H_2O$ to 90:10 MeOH/$H_2O$, 0.2% $H_3PO_4$).

Method C: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Method D: Waters Acquity UPLC BEH C18, 2.1×50 mm, 1.7-µm particles; Mobile Phase A: 5:95 acetonitrile:water with 0.1% TFA; Mobile Phase B: 95:5 acetonitrile:water with 0.1% TFA; Temperature: 50° C.; Gradient: 0-100% B over 3 minutes, then a 0.75-minute hold at 100% B; Flow: 1.11 mL/min.

A majority of mass spectra runs were: LCMS(ESI) m/z: [M+H]$^+$ PHENOMENEX® Luna C18 (2×30 mm) (2 min gradient 90% $H_2O$/10% MeOH/0.1% TFA to 90% MeOH/10% $H_2O$/0.1% TFA) (or) BEH C18 2.1×50 mm–2 min gradient from 0-100% B. (A: 90/10/0.1 $H_2O$/ACN/TFA; B: 90/10/0.1 ACN/$H_2O$/TFA).

Intermediate 1

2-(5-Chloro-2-(1H-tetrazol-1-yl)phenyl)ethanamine

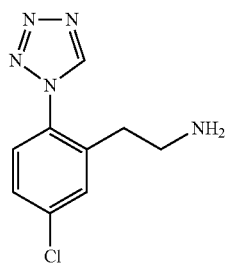 [SMILES: NCCc1cc(Cl)ccc1-n1cnnn1]

Intermediate 1: Intermediate 1 was prepared according the literature procedure (Pinto, D. J. P. et al., WO 08/157162). $^1$H NMR (CDCl$_3$) δ: 9.11 (s, 1H), 7.54-7.46 (dd, J=1.2 and 8.5 Hz, 1H), 7.39-7.23 (m, 2H). MS(ESI) m/z: 224.2 (M+H)$^+$.

Intermediate 2 tert-Butyl ((4-aminopiperidin-1-yl)((tert-butoxycarbonyl)amino)methylene)carbamate

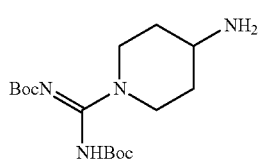

Intermediate 2A: Benzyl N-{1-[(1Z)-{[(tert-butoxy)carbonyl]amino}({[(tert-butoxy)carbonyl]imino})methyl]piperidin-4-yl}carbamate: To a solution of benzyl piperidin-4-ylcarbamate (359 mg, 1.531 mmol) in DMF (15 ml) was added tert-butyl (((tert-butoxycarbonyl)amino)(1H-pyrazol-1-yl)methylene)carbamate (475 mg, 1.531 mmol) and Hunig's base (3.2 ml, 18.37 mmol). The mixture was stirred at rt overnight. LCMS showed the desired mass for the product. The mixture was diluted with EtOAc, washed with aq. sat. NaHCO$_3$ and brine. The organic layer was concentrated and purified by silica gel chromatography to give Intermediate 2A (670 mg, 1.406 mmol, 92% yield). MS(ESI) m/z: 477.4 (M+H)$^+$.

Intermediate 2: To a solution of Intermediate 2A (700 mg, 1.469 mmol) in EtOH (29 ml) added palladium on carbon (156 mg, 0.147 mmol). The reaction mixture was stirred under H$_2$ balloon for 4 h. The reaction mixture was filter through CELITE® and concentrated. The product was pure enough for the next reaction. $^1$H NMR (400 MHz, CDCl$_3$)

δ 10.18 (br. s., 1H), 3.34-3.18 (m, 1H), 3.03 (br. s., 4H), 1.93-1.72 (m, 4H), 1.66-1.26 (m, 18H). MS(ESI) m/z: 343.4 (M+H)+.

Intermediate 3 tert-Butyl ((4-(aminomethyl)piperidin-1-yl)((tert-butoxycarbonyl)amino) methylene)carbamate

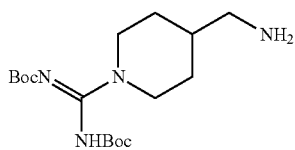

Intermediate 3 was prepared using a procedure analogous to Intermediate 2 except that benzyl piperidin-4-ylcarbamate was replaced with benzyl (piperidin-4-ylmethyl)carbamate. $^1$H NMR (400 MHz, CD$_3$OD) δ 4.13 (d, J=11.9 Hz, 2H), 3.06-2.68 (m, 5H), 1.81 (d, J=12.8 Hz, 2H), 1.58-1.03 (m, 20H). MS(ESI) m/z: 357.3 (M+H)+.

Intermediate 4 tert-Butyl ((4-(2-aminoethyl)piperidin-1-yl)((tert-butoxycarbonyl)amino) methylene)carbamate

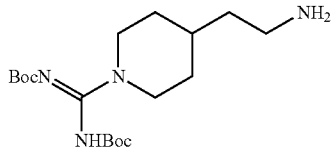

Intermediate 4 was prepared using a procedure analogous to Intermediate 2 except that benzyl piperidin-4-ylcarbamate was replaced with benzyl (2-(piperidin-4-yl)ethyl)carbamate. $^1$H NMR (400 MHz, CDCl$_3$) δ 4.35-3.86 (m, 2H), 2.91 (br. s., 4H), 1.87-1.54 (m, 5H), 1.51-1.39 (m, 18H), 1.36-1.12 (m, 2H). MS(ESI) m/z: 371.2 (M+H)+.

Example 1

(±)-Methyl N-[8-({2-[5-chloro-2-(1H-1,2,3,4-tetrazol-1-yl)phenyl]ethyl}carbamoyl)-2,10-dioxo-1,2,3,4,5,6,7,8,9,10-decahydro-1,9-benzodiazacyclododecin-13-yl]carbamate

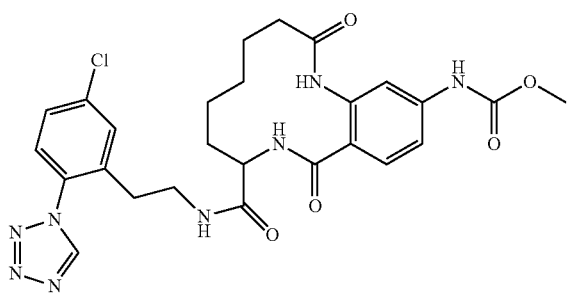 [SMILES: COC(=O)Nc1ccc2c(c1)NC(=O)CCCCCC(C(=O)NCCc1cc(Cl)ccc1-n1cnnn1)NC2=O]

1A. (±) Methyl 2-aminopent-4-enoate, HCl salt: To a suspension of 2-aminopent-4-enoic acid (1.9 g, 16.50 mmol) in MeOH (50 mL) was added thionyl chloride (2.168 mL, 29.7 mmol) dropwise at 0° C. Upon addition, the cooling bath was removed and the reaction was stirred at rt overnight. The solvent was removed to give a white solid. $^1$H NMR (400 MHz, CD$_3$OD) δ 5.79 (dd, J=10.1, 7.5 Hz, 1H), 5.42-5.11 (m, 2H), 3.84 (s, 3H), 2.90-2.35 (m, 2H).

1B. (±) Methyl 2-(2-amino-4-nitrobenzamido)pent-4-enoate: To a solution of 2-amino-4-nitrobenzoic acid (2.199 g, 12.08 mmol) in DMF (24 ml) was added 1A (2 g, 12.08 mmol), HOBT (0.925 g, 6.04 mmol), DIEA (6.33 ml, 36.2 mmol) and EDC (2.55 g, 13.28 mmol) at rt. The reaction was stirred under Ar at rt for 16 hrs. The reaction mixture was diluted with EtOAc, washed with 1M HCl, aq. sat. NaHCO$_3$ and brine. The organic phase was dried over magnesium sulfate, filtered and concentrated. The crude product was purified by silica gel chromatography to give 1B (1.7 g, 5.80 mmol, 48.0% yield). $^1$H NMR (400 MHz, CDCl$_3$) δ 7.58-7.43 (m, 3H), 6.63 (d, J=6.8 Hz, 1H), 5.88-5.67 (m, 3H), 5.22-5.17 (m, 1H), 4.92-4.79 (m, 1H), 3.84 (s, 3H), 2.70 (dt, J=19.3, 6.5 Hz, 2H). MS(ESI) m/z: 293.9 (M+H)+.

1C. (±) Methyl 2-(4-nitro-2-(pent-4-enamido)benzamido) pent-4-enoate: To a solution of 1B (220 mg, 0.750 mmol) in ethyl acetate (15 ml) was added pent-4-enoic acid (150 mg, 1.50 mmol), DIEA (655 µl, 3.75 mmol) and 2,4,6-tripropyl-1,3,5,2,4,6-trioxatriphosphinane 2,4,6-trioxide (1.3 ml, 2.250 mmol) at rt. The reaction was stirred under Ar at 50° C. for 16 h. Water (15 mL) was added to quench the reaction. The reaction was diluted with EtOAc and organic layer was dried over Na$_2$SO$_4$. The organic layer was filtered and concentrated. The crude product was purified by silica gel chromatography to give 1C (220 mg, 0.586 mmol, 78% yield). $^1$H NMR (400 MHz, CDCl$_3$) δ 10.87 (br. s., 1H), 9.53 (d, J=2.0 Hz, 1H), 7.92 (dd, J=8.7, 2.1 Hz, 1H), 7.66 (d, J=8.8 Hz, 1H), 6.80 (d, J=7.3 Hz, 1H), 5.88 (dd, J=16.8, 10.5 Hz, 1H), 5.80-5.63 (m, 1H), 5.28-4.98 (m, 4H), 4.84 (d, J=7.0 Hz, 1H), 3.84 (s, 3H), 2.93-2.62 (m, 2H), 2.58-2.43 (m, 4H). MS(ESI) m/z: 376.2 (M+H)+.

1D. (±) Methyl 13-nitro-2,10-dioxo-1,2,3,4,7,8,9,10-octahydrobenzo[b][1,5]diazacyclododecine-8-carboxylate: To a vial was added 1C (170 mg, 0.453 mmol) and DCM (90 ml). The clear solution was degassed with Ar for 15 min, then Grubbs II catalyst (154 mg, 0.181 mmol) was added. The reaction was stirred at 40° C. for 16 h. LCMS showed the desired mass for the product. Purification by silica gel chromatography gave 1D (140 mg, 0.403 mmol, 89% yield). MS(ESI) m/z: 348.3 (M+H)+.

1E. (±)-Methyl 13-amino-2,10-dioxo-1,2,3,4,5,6,7,8,9,10-decahydrobenzo[b][1,5]diazacyclododecine-8-carboxylate: To a solution of 1D (34 mg, 0.098 mmol) in EtOH (1.9 ml) was added palladium on carbon (10.42 mg, 9.79 µmol). The reaction mixture stirred under H$_2$ (1 atm) for 4 h. The reaction mixture was filtered through CELITE® and concentrated. The crude mixture was used in the next reaction without further purification. MS(ESI) m/z: 320.3 (M+H)+.

1F. (±)-Methyl 13-((methoxycarbonyl)amino)-2,10-dioxo-1,2,3,4,5,6,7,8,9,10-decahydrobenzo[b][1,5]diazacyclododecine-8-carboxylate: To a solution of 1E (25 mg, 0.078 mmol) in DCM (783 µl) was added pyridine (31.7 µl. 0.391 mmol) and methyl chloroformate (6.06 µl, 0.078 mmol) at 0° C. The reaction was stirred under Ar at 0° C. for 30 min. The reaction mixture was then diluted with EtOAc, washed with 1M HCl, aq. sat. NaHCO$_3$ and brine. The organic phase was dried over magnesium sulfate, filtered and concentrated. The crude product was purified by silica gel chromatography to give 1F (20 mg, 68%). MS(ESI) m/z: 378.1 (M+H)+.

1G. (±)-13-((Methoxycarbonyl)amino)-2,10-dioxo-1,2,3,4,5,6,7,8,9,10-decahydrobenzo[b][1,5]diazacyclododecine-8-carboxylic acid: To a solution of 1F (30 mg, 0.079 mmol) in THF (4 mL) and water (2 mL) was added LiOH (0.199 mL, 0.397 mmol) at 0° C. The reaction was stirred under Ar at 0° C. After 1 h, LCMS showed the reaction was completed. 1 eq. of 1.0 N HCl solution was added to the reaction mixture and the solvent was removed to leave a white solid as the crude product, which was used as it was in the next step without further purification. MS(ESI) m/z: 364.1.1 (M+H)+.

Example 1: To a solution of 1G (35 mg, 0.096 mmol) in DMF (963 μl) was added Intermediate 1 (50.1 mg, 0.193 mmol), HATU (73.2 mg, 0.193 mmol) and DIEA (336 μl, 1.926 mmol) at rt. The reaction was stirred under Ar at rt overnight. The crude product was purified by Prep HPLC. $^1$H NMR (400 MHz, DMSO-d$_6$) δ 9.94 (s, 1H), 9.79 (s, 1H), 9.69 (s, 1H), 8.02 (br. s., 1H), 7.65-7.50 (m, 4H), 7.45-7.23 (m, 3H), 4.30-4.07 (m, 1H), 3.68 (s, 3H), 2.40-2.27 (m, 4H), 2.23-2.09 (m, 1H), 1.88-1.08 (m, 9H). MS(ESI) m/z: 569.1 (M+H)+. Analytical HPLC (Method A): RT=6.6 min.

Example 2 (Enantiomer 1) and Example 3 (Enantiomer 2)

Methyl N-[8-({2-[5-chloro-2-(1H-1,2,3,4-tetrazol-1-yl)phenyl]ethyl}carbamoyl)-2,10-dioxo-1,2,3,4,5,6,7,8,9,10-decahydro-1,9-benzodiazacyclododecin-13-yl]carbamate (enantiomer 1), and Methyl N-[8-({2-[5-chloro-2-(1H-1,2,3,4-tetrazol-1-yl)phenyl]ethyl}carbamoyl)-2,10-dioxo-1,2,3,4,5,6,7,8,9,10-decahydro-1,9-benzodiazacyclododecin-13-yl]carbamate (enantiomer 2)

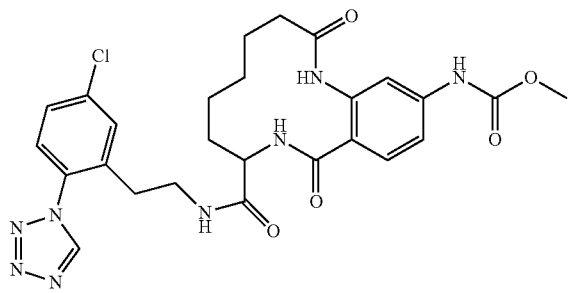 [SMILES: COC(=O)Nc1ccc2c(c1)NC(=O)CCCCCC(C(=O)NCCc1cc(Cl)ccc1-n1cnnn1)NC2=O]

Example 2 and Example 3: The racemic mixture of Example 1 was separated by chiral Prep. SFC to provide Example 2 and Example 3 as single enantiomers.

Example 2: Enantiomer 1 (the early eluting enantiomer), $^1$H NMR (400 MHz, DMSO-d$_6$) δ 10.11-9.74 (m, 2H), 9.69 (s, 1H), 8.01 (s, 1H), 7.70-7.50 (m, 4H), 7.45-7.18 (m, 3H), 4.25 (br. s., 1H), 3.68 (s, 3H), 3.24-3.02 (m, 2H), 2.44-2.30 (m, 2H), 2.23-2.05 (m, 1H), 1.79-1.18 (m, 9H). MS(ESI) m/z: 569.1 (M+H)+. Analytical HPLC (Method A): RT=6.6 min.

Example 3: Enantiomer 2 (the late eluting enantiomer), $^1$H NMR (400 MHz, DMSO-d$_6$) δ 9.93 (s, 1H), 9.80 (s, 1H), 9.69 (s, 1H), 8.01 (s, 1H), 7.70-7.50 (m, 4H), 7.45-7.18 (m, 3H), 4.25 (br. s., 1H), 3.69 (s, 3H), 3.24-3.02 (m, 2H), 2.44-2.30 (m, 2H), 2.23-2.05 (m, 1H), 1.79-1.18 (m, 9H). MS(ESI) m/z: 569.1 (M+H)+. Analytical HPLC (Method A): RT=6.6 min.

Example 4

(±)-Methyl N-{8-[(1-carbamimidoylpiperidin-4-yl)carbamoyl]-2,10-dioxo-1,2,3,4,5,6,7,8,9,10-decahydro-1,9-benzodiazacyclododecin-13-yl}carbamate

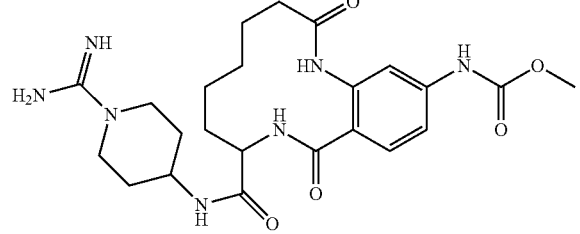

Example 4: To a solution of 1G (35 mg, 0.096 mmol) in DMF (963 μl) was added Intermediate 2 (66.0 mg, 0.193 mmol), HATU (73.2 mg, 0.193 mmol) and DIEA (336 μl, 1.926 mmol) at rt. The reaction was stirred under Ar at rt overnight. The crude product was purified by reverse phase prep-HPLC. The residue was dissolved in 3 ml of DCM and 1 ml of TFA. After 2 h, the solvent was removed and afforded Example 4 (2 TFA salt, 7 mg, 9.29 μmol, 9.65% yield). $^1$H NMR (400 MHz, CD$_3$OD) δ 9.57 (s, 1H), 8.15 (d, J=7.0 Hz, 1H), 7.92-7.76 (m, 1H), 7.51-7.33 (m, 3H), 4.49 (br. s., 1H), 4.04-3.79 (m, 3H), 3.74 (s, 3H), 3.20 (br. s., 4H), 2.55-2.43 (m, 1H), 2.39-2.28 (m, 1H), 1.98-1.25 (s, 10H). MS(ESI) m/z: 488.2 (M+H)+. Analytical HPLC (Method A): RT=2.8 min.

Example 5

(±)-Methyl N-(8-{[(1-carbamimidoylpiperidin-4-yl)methyl]carbamoyl}-2,10-dioxo-1,2,3,4,5,6,7,8,9,10-decahydro-1,9-benzodiazacyclododecin-13-yl)carbamate

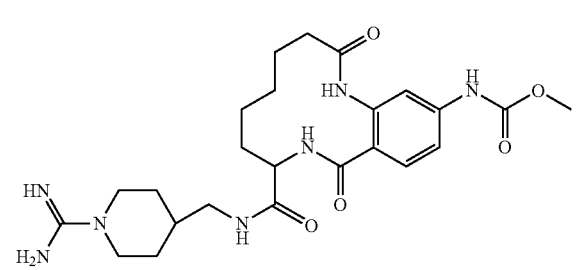 [SMILES: COC(=O)Nc1ccc2c(c1)NC(=O)CCCCCC(C(=O)NCC1CCN(C(=N)N)CC1)NC2=O]

Example 5 was prepared using a procedure analogous to Example 4 except that Intermediate 2 was replaced with Intermediate 3. $^1$H NMR (400 MHz, CD$_3$OD) δ 9.58 (s, 1H), 8.31-8.02 (m, 1H), 7.94-7.81 (m, 1H), 7.57-7.35 (m, 3H), 7.18 (br. s., 1H), 4.45 (d, J=7.0 Hz, 1H), 3.88 (d, J=12.8 Hz, 2H), 3.75 (s, 3H), 3.21-2.93 (m, 5H), 2.63-2.44 (m, 1H), 2.41-2.25 (m, 1H), 1.95-1.17 (m, 12H). MS(ESI) m/z: 502.3 (M+H)+. Analytical HPLC (Method A): RT=3.1 min.

Example 6

(±)-Methyl N-(8-{[2-(1-carbamimidoylpiperidin-4-yl)ethyl]carbamoyl}-2,10-dioxo-1,2,3,4,5,6,7,8,9,10-decahydro-1,9-benzodiazacyclododecin-13-yl)carbamate

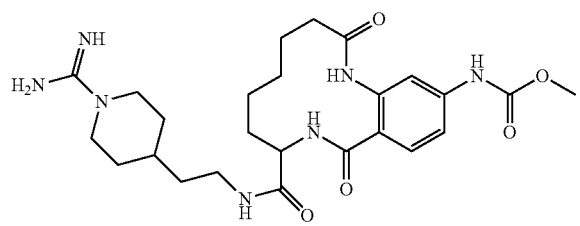 [SMILES: COC(=O)Nc1ccc2c(c1)NC(=O)CCCCCC(C(=O)NCCC1CCN(C(=N)N)CC1)NC2=O]

Example 6 was prepared using a procedure analogous to Example 4 except that Intermediate 2 was replaced with Intermediate 4. $^1$H NMR (400 MHz, CD$_3$OD) δ 7.53-7.35 (m, 3H), 4.45 (dd, J=10.3, 3.3 Hz, 1H), 3.86 (d, J=13.6 Hz, 2H), 3.75 (s, 3H), 3.26 (td, J=6.9, 2.3 Hz, 2H), 3.05 (t, J=13.0 Hz, 2H), 2.49 (dd, J=8.0, 4.5 Hz, 1H), 2.41-2.23 (m, 1H), 1.93-1.77 (m, 5H), 1.75-1.42 (m, 11H), 1.38-1.09 (m, 3H). MS(ESI) m/z: 516.2 (M+H)$^+$. Analytical HPLC (Method A): RT=3.4 min.

Example 7

(±)-Methyl N-{2,10-dioxo-8-[(2-oxo-1,2,3,4-tetrahydroquinolin-3-yl)carbamoyl]-1,2,3,4,5,6,7,8,9,10-decahydro-1,9-benzodiazacyclododecin-13-yl}carbamate

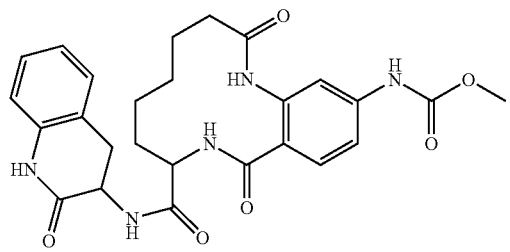 [SMILES: COC(=O)Nc1ccc2c(c1)NC(=O)CCCCCC(C(=O)NC1Cc3ccccc3NC1=O)NC2=O]

Example 7 was prepared using a procedure analogous to Example 4 except that Intermediate 2 was replaced with 3-amino-3,4-dihydroquinolin-2(1H)-one. $^1$H NMR (500 MHz, DMSO-d$_6$) δ 10.33 (d, J=12.7 Hz, 1H), 9.91 (s, 1H), 9.72 (d, J=11.3 Hz, 1H), 7.48-7.31 (m, 3H), 7.27-7.10 (m, 2H), 7.01-6.78 (m, 2H), 4.62-4.32 (m, 2H), 3.70 (s, 3H), 3.15-3.00 (m, 1H), 2.89 (s, 1H), 2.46-2.34 (m, 1H), 2.26-2.14 (m, 1H), 1.92-1.32 (m, 8H). MS(ESI) m/z: 508.1 (M+H)$^+$. Analytical HPLC (Method C): RT=1.2 min.

Example 8

(±)-Methyl N-(8-{[(5-chloro-1-benzothiophen-3-yl)methyl]carbamoyl}-2,10-dioxo-1,2,3,4,5,6,7,8,9,10-decahydro-1,9-benzodiazacyclododecin-13-yl)carbamate

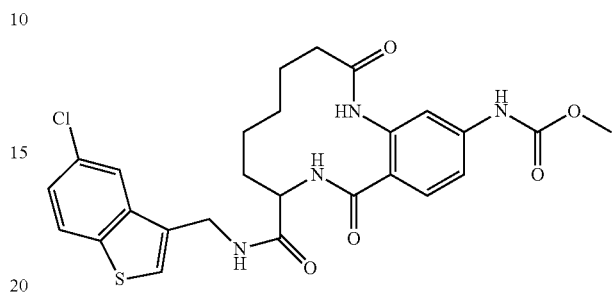

Example 8 was prepared using a procedure analogous to Example 4 except that Intermediate 2 was replaced with (5-chlorobenzo[b]thiophen-3-yl)methanamine. $^1$H NMR (500 MHz, DMSO-d$_6$) δ 9.91 (s, 1H), 9.67 (br. s., 1H), 8.62-8.42 (m, 1H), 8.03 (d, J=8.5 Hz, 1H), 7.92 (d, J=1.8 Hz, 1H), 7.75-7.61 (m, 2H), 7.47-7.27 (m, 4H), 4.60-4.33 (m, 3H), 3.69 (s, 3H), 2.44-2.32 (m, 1H), 2.24-2.08 (m, 1H), 1.76-1.27 (m, 8H).

Example 9

(±)-Methyl N-{8-[3-(3-chlorophenyl)pyrrolidine-1-carbonyl]-2,10-dioxo-1,2,3,4,5,6,7,8,9,10-decahydro-1,9-benzodiazacyclododecin-13-yl}carbamate

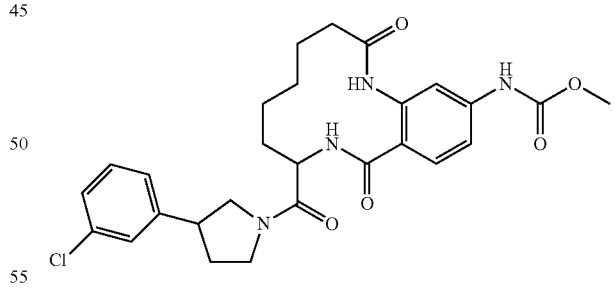

Example 9 was prepared using a procedure analogous to Example 4 except that Intermediate 2 was replaced with 3-(3-chlorophenyl)pyrrolidine. $^1$H NMR (500 MHz, DMSO-d$_6$) δ 9.93 (br. s., 1H), 9.74 (br. s., 1H), 7.89-7.66 (m, 1H), 7.51-7.22 (m, 7H), 4.61 (d, J=19.8 Hz, 1H), 4.23-3.77 (m, 2H), 3.69 (s, 3H), 3.62-3.45 (m, 2H), 3.29-3.12 (m, 1H), 2.47-1.89 (m, 4H), 1.81-1.28 (m, 8H).

Example 10

(±)-Methyl N-{8-[3-(3-methoxyphenyl)piperidine-1-carbonyl]-2,10-dioxo-1,2,3,4,5,6,7,8,9,10-decahydro-1,9-benzodiazacyclododecin-13-yl}carbamate

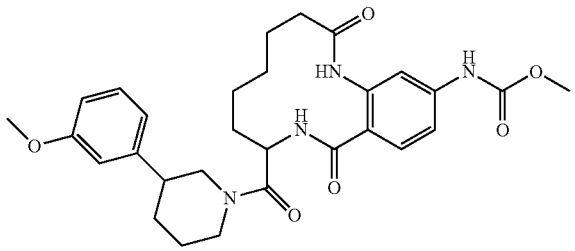

Example 10 was prepared using a procedure analogous to Example 4 except that Intermediate 2 was replaced with (5-chlorobenzo[b]thiophen-3-yl)methanamine. $^1$H NMR (500 MHz, DMSO-d$_6$) δ 9.92 (br. s., 1H), 9.84-9.56 (m, 1H), 7.78-7.55 (m, 1H), 7.47-7.12 (m, 4H), 6.97-6.71 (m, 3H), 4.86 (br. s., 1H), 4.51-4.25 (m, 1H), 4.08-3.86 (m, 1H), 3.74 (s, 3H), 3.69 (s, 3H), 3.27-3.06 (m, 1H), 2.77-2.56 (m, 2H), 2.45-2.32 (m, 1H), 2.24-2.08 (m, 1H), 1.96-1.31 (m, 14H). MS(ESI) m/z: 537.4 (M+H)$^+$. Analytical HPLC (Method C): RT=2.5 min.

Example 11 (Diastereomeric Mixture)

(±)-Methyl N-[8-({2-[5-chloro-2-(1H-1,2,3,4-tetrazol-1-yl)phenyl]ethyl}carbamoyl)-4-methyl-2,10-dioxo-1,2,3,4,5,6,7,8,9,10-decahydro-1,9-benzodiazacyclododecin-13-yl]carbamate

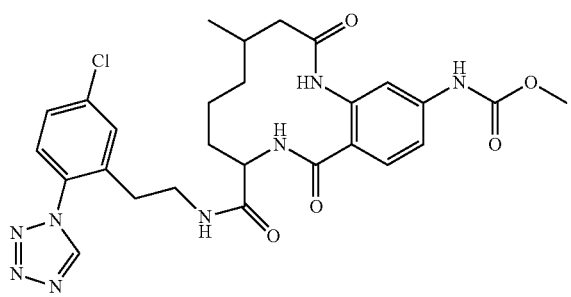 [SMILES: COC(=O)Nc1ccc2c(c1)NC(=O)CC(C)CCCC(C(=O)NCCc1cc(Cl)ccc1-n1cnnn1)NC2=O]

Example 11 was prepared using a procedure analogous to Example 1 except that pent-4-enoic acid was replaced with 3-methylpent-4-enoic acid in step 1C. MS(ESI) m/z: 583.2 (M+H)$^+$.

The major racemate pair: $^1$H NMR (400 MHz, DMSO-d$_6$) δ 9.90 (s, 1H), 9.79 (s, 1H), 9.72-9.64 (m, 1H), 7.99 (t, J=5.7 Hz, 1H), 7.67-7.55 (m, 4H), 7.37 (s, 2H), 7.32-7.28 (m, 1H), 4.14 (br. s., 1H), 3.69 (s, 3H), 3.26-3.05 (m, 2H), 2.55 (s, 2H), 2.43-2.28 (m, 1H), 2.18-2.08 (m, 1H), 2.06-1.86 (m, 1H), 1.59-1.38 (m, 3H), 1.33-1.13 (m, 3H), 0.97 (d, J=6.8 Hz, 3H).

The minor racemate pair: $^1$H NMR (400 MHz, DMSO-d$_6$) δ 9.91 (s, 1H), 9.80 (s, 1H), 9.60 (s, 1H), 7.98 (s, 1H), 7.65-7.56 (m, 3H), 7.53-7.46 (m, 1H), 7.35 (s, 3H), 4.44-4.28 (m, 1H), 3.69 (s, 3H), 3.26-3.05 (m, 2H), 2.13 (br. s., 4H), 1.75-1.47 (m, 3H), 1.45-1.06 (m, 4H), 0.94 (d, J=6.2 Hz, 3H). MS(ESI) m/z: 583.2 (M+H)+.

Analytical HPLC (Method A): RT=6.5 min (the minor racemate pair), RT=6.8 min (the major racemate pair).

Example 12 (Enantiomer 1), Example 13 (Enantiomer 2), Example 14 (Enantiomer 3), and Example 15 (Enantiomer 4)

Methyl N-[8-({2-[5-chloro-2-(1H-1,2,3,4-tetrazol-1-yl)phenyl]ethyl}carbamoyl)-4-methyl-2,10-dioxo-1,2,3,4,5,6,7,8,9,10-decahydro-1,9-benzodiazacyclododecin-13-yl]carbamate

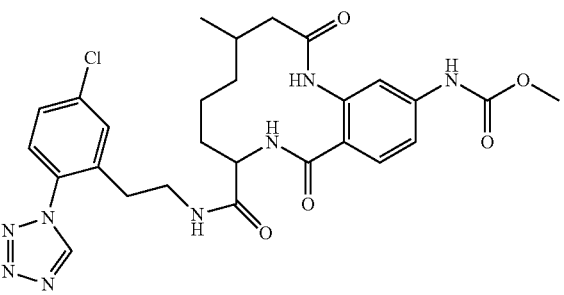 [SMILES: COC(=O)Nc1ccc2c(c1)NC(=O)CC(C)CCCC(C(=O)NCCc1cc(Cl)ccc1-n1cnnn1)NC2=O]

Example 12, Example 13, Example 14 and Example 15: The diastereomeric mixture of Example 11 was separated by chiral Prep. SFC to give Example 12, Example 13, Example 14 and Example 15 as single enantiomers.

Example 12: enantiomer 1 (the first eluting enantiomer), $^1$H NMR (400 MHz, DMSO-d$_6$) δ 9.90 (s, 1H), 9.79 (s, 1H), 9.72-9.64 (m, 1H), 7.99 (t, J=5.7 Hz, 1H), 7.67-7.55 (m, 4H), 7.37 (s, 2H), 7.32-7.28 (m, 1H), 4.14 (br. s., 1H), 3.69 (s, 3H), 3.26-3.05 (m, 2H), 2.55 (s, 2H), 2.43-2.28 (m, 1H), 2.18-2.08 (m, 1H), 2.06-1.86 (m, 1H), 1.59-1.38 (m, 3H), 1.33-1.13 (m, 3H), 0.97 (d, J=6.8 Hz, 3H). MS(ESI) m/z: 583.2 (M+H)$^+$. Analytical HPLC (Method A): RT=6.8 min.

Example 13: enantiomer 2 (the second eluting enantiomer), $^1$H NMR (400 MHz, DMSO-d$_6$) δ 9.91 (s, 1H), 9.80 (s, 1H), 9.60 (s, 1H), 7.98 (s, 1H), 7.65-7.56 (m, 3H), 7.53-7.46 (m, 1H), 7.35 (s, 3H), 4.44-4.28 (m, 1H), 3.69 (s, 3H), 3.26-3.05 (m, 2H), 2.13 (br. s., 4H), 1.75-1.47 (m, 3H), 1.45-1.06 (m, 4H), 0.94 (d, J=6.2 Hz, 3H). MS(ESI) m/z: 583.2 (M+H)$^+$. Analytical HPLC (Method A): RT=6.4 min.

Example 14: enantiomer 3 (the third eluting enantiomer), $^1$H NMR (400 MHz, DMSO-d$_6$) δ 9.90 (s, 1H), 9.79 (s, 1H), 9.72-9.64 (m, 1H), 7.99 (t, J=5.7 Hz, 1H), 7.67-7.55 (m, 4H), 7.37 (s, 2H), 7.32-7.28 (m, 1H), 4.14 (br. s., 1H), 3.69 (s, 3H), 3.26-3.05 (m, 2H), 2.55 (s, 2H), 2.43-2.28 (m, 1H), 2.18-2.08 (m, 1H), 2.06-1.86 (m, 1H), 1.59-1.38 (m, 3H), 1.33-1.13 (m, 3H), 0.97 (d, J=6.8 Hz, 3H). MS(ESI) m/z: 583.2 (M+H)$^+$. Analytical HPLC (Method A): RT=6.8 min.

Example 15: enantiomer 4 (the fourth eluting enantiomer), $^1$H NMR (400 MHz, DMSO-d$_6$) δ 9.91 (s, 1H), 9.80 (s, 1H), 9.60 (s, 1H), 7.98 (s, 1H), 7.65-7.56 (m, 3H), 7.53-7.46 (m, 1H), 7.35 (s, 3H), 4.44-4.28 (m, 1H), 3.69 (s, 3H), 3.26-3.05 (m, 2H), 2.13 (br. s., 4H), 1.75-1.47 (m, 3H), 1.45-1.06 (m, 4H), 0.94 (d, J=6.2 Hz, 3H). MS(ESI) m/z: 583.2 (M+H)$^+$. Analytical HPLC (Method A): RT=6.4 min.

Example 16 (Racemate 1) and Example 17 (Racemate 2)

(±)-Methyl N-[8-({2-[5-chloro-2-(1H-1,2,3,4-tetrazol-1-yl)phenyl]ethyl}carbamoyl)-3-methyl-2,10-dioxo-1,2,3,4,5,6,7,8,9,10-decahydro-1,9-benzodiazacyclododecin-13-yl]carbamate

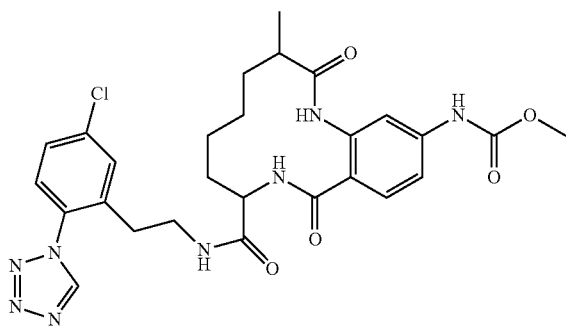 [SMILES: COC(=O)Nc1ccc2c(c1)NC(=O)C(C)CCCCC(C(=O)NCCc1cc(Cl)ccc1-n1cnnn1)NC2=O]

Example 16 and Example 17 were prepared using a procedure analogous to Example 1 except that pent-4-enoic acid was replaced with 2-methylpent-4-enoic acid in step 1C.

Example 16: $^1$H NMR (400 MHz, DMSO-$d_6$) δ 9.91 (s, 1H), 9.80 (s, 1H), 9.45 (s, 1H), 7.99 (br. s., 1H), 7.77 (d, J=8.4 Hz, 1H), 7.69-7.52 (m, 3H), 7.46-7.22 (m, 3H), 4.30-4.13 (m, 1H), 3.68 (s, 3H), 3.18-3.03 (m, 3H), 2.46-2.24 (m, 2H), 1.57 (br. s., 4H), 1.24 (br. s., 4H), 1.01 (d, J=6.6 Hz, 3H). MS(ESI) m/z: 583.3 (M+H)$^+$. Analytical HPLC (Method A): RT=6.3 min.

Example 17: $^1$H NMR (400 MHz, CD$_3$OD) δ 9.54 (s, 1H), 7.60 (d, J=2.0 Hz, 1H), 7.50 (d, J=2.6 Hz, 2H), 7.47-7.35 (m, 4H), 7.11 (d, J=8.1 Hz, 1H), 4.29 (s, 1H), 3.74 (s, 3H), 2.68 (t, J=6.3 Hz, 3H), 2.56-2.39 (m, 1H), 2.25-2.01 (m, 1H), 1.89-1.61 (m, 2H), 1.57-1.37 (m, 2H), 1.35-1.26 (m, 2H), 1.22-1.18 (m, 3H), 1.08-0.99 (m, 1H), 0.77-0.61 (m, 1H). MS(ESI) m/z: 583.4 (M+H)$^+$. Analytical HPLC (Method A): RT=6.0 min.

Example 18 (Enantiomer 1), Example 19 (Enantiomer 2), Example 20 (Enantiomer 3), and Example 21 (Enantiomer 4)

Methyl N-[8-({2-[5-chloro-2-(1H-1,2,3,4-tetrazol-1-yl)phenyl]ethyl}carbamoyl)-3-methyl-2,10-dioxo-1,2,3,4,5,6,7,8,9,10-decahydro-1,9-benzodiazacyclododecin-13-yl]carbamate

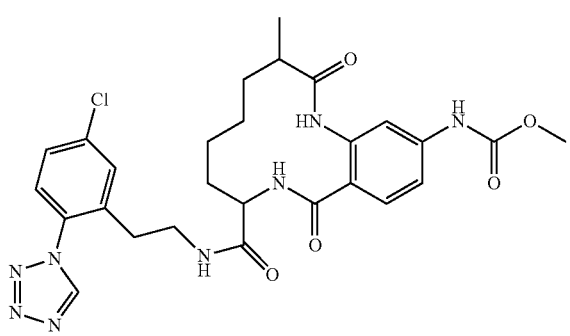 [SMILES: COC(=O)Nc1ccc2c(c1)NC(=O)C(C)CCCCC(C(=O)NCCc1cc(Cl)ccc1-n1cnnn1)NC2=O]

Example 18 and Example 19: The racemic mixture Example 16 was separated by chiral Prep. SFC to give Example 18 and Example 19 as single enantiomers.

Example 18: enantiomer 1 (the early eluting enantiomer), $^1$H NMR (400 MHz, DMSO-$d_6$) δ 9.91 (s, 1H), 9.80 (s, 1H), 9.45 (s, 1H), 7.99 (br. s., 1H), 7.77 (d, J=8.4 Hz, 1H), 7.69-7.52 (m, 3H), 7.46-7.22 (m, 3H), 4.30-4.13 (m, 1H), 3.68 (s, 3H), 3.18-3.03 (m, 3H), 2.46-2.24 (m, 2H), 1.57 (br. s., 4H), 1.24 (br. s., 4H), 1.01 (d, J=6.6 Hz, 3H). MS(ESI) m/z: 583.3 (M+H). Analytical HPLC (Method A): RT=6.3 min.

Example 19: enantiomer 2 (the late eluting enantiomer), $^1$H NMR (400 MHz, DMSO-$d_6$) δ 9.91 (s, 1H), 9.80 (s, 1H), 9.45 (s, 1H), 7.99 (br. s., 1H), 7.77 (d, J=8.4 Hz, 1H), 7.69-7.52 (m, 3H), 7.46-7.22 (m, 3H), 4.30-4.13 (m, 1H), 3.68 (s, 3H), 3.18-3.03 (m, 3H), 2.46-2.24 (m, 2H), 1.57 (br. s., 4H), 1.24 (br. s., 4H), 1.01 (d, J=6.6 Hz, 3H). MS(ESI) m/z: 583.3 (M+H)$^+$. Analytical HPLC (Method A): RT=6.3 min.

Example 20 and Example 21: The racemic mixture Example 17 was separated by chiral Prep. SFC to give Example 20 and Example 21 as single enantiomers.

Example 20: enantiomer 3 (the early eluting enantiomer), $^1$H NMR (400 MHz, CD$_3$OD) δ 9.54 (s, 1H), 7.60 (d, J=2.0 Hz, 1H), 7.50 (d, J=2.6 Hz, 2H), 7.47-7.35 (m, 4H), 7.11 (d, J=8.1 Hz, 1H), 4.29 (s, 1H), 3.74 (s, 3H), 2.68 (t, J=6.3 Hz, 3H), 2.56-2.39 (m, 1H), 2.25-2.01 (m, 1H), 1.89-1.61 (m, 2H), 1.57-1.37 (m, 2H), 1.35-1.26 (m, 2H), 1.22-1.18 (m, 3H), 1.08-0.99 (m, 1H), 0.77-0.61 (m, 1H). MS(ESI) m/z: 583.4 (M+H)$^+$. Analytical HPLC (Method A): RT=6.0 min.

Example 21: enantiomer 4 (the late eluting enantiomer), $^1$H NMR (400 MHz, CD$_3$OD) δ 9.54 (s, 1H), 7.60 (d, J=2.0 Hz, 1H), 7.50 (d, J=2.6 Hz, 2H), 7.47-7.35 (m, 4H), 7.11 (d, J=8.1 Hz, 1H), 4.29 (s, 1H), 3.74 (s, 3H), 2.68 (t, J=6.3 Hz, 3H), 2.56-2.39 (m, 1H), 2.25-2.01 (m, 1H), 1.89-1.61 (m, 2H), 1.57-1.37 (m, 2H), 1.35-1.26 (m, 2H), 1.22-1.18 (m, 3H), 1.08-0.99 (m, 1H), 0.77-0.61 (m, 1H). MS(ESI) m/z: 583.4 (M+H)$^-$. Analytical HPLC (Method A): RT=6.0 min.

Example 22

(E/Z)-(±)-Methyl N-[8-({2-[5-chloro-2-(1H-1,2,3,4-tetrazol-1-yl)phenyl]ethyl}carbamoyl)-2,10-dioxo-1,2,3,4,7,8,9,10-octahydro-1,9-benzodiazacyclododecin-13-yl]carbamate

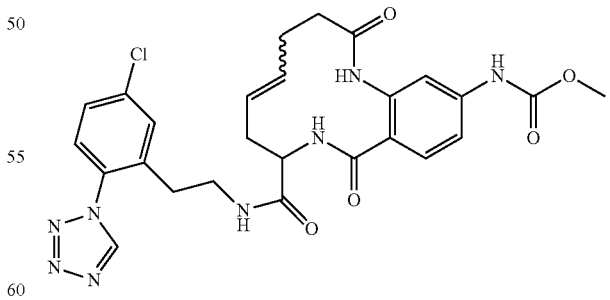

22A. (E/Z)-Methyl 13-amino-2,10-dioxo-1,2,3,4,7,8,9,10-octahydrobenzo[b][1,5]diazacyclododecine-8-carboxylate: To a solution of 1D (140 mg, 0.403 mmol) in methanol (30 mL) was added ammonium chloride (108 mg, 2.015 mmol) and zinc (132 mg, 2.015 mmol) at 0° C. The reaction was stirred under Ar at rt for 16 hrs. LCMS showed the reaction was complete. The solid was filtered off and the filtrate was concentrated to give a white solid, which was used in the next step without further purification. MS(ESI) m/z: 318.3 (M+H)+.

Example 22 was prepared using a procedure analogous to Example 1 except that 1F was replaced with 22A in step 1G. MS(ESI) m/z: 567.3 (M+H)+. $^1$H NMR (400 MHz, DMSO-$d_6$) δ 9.94-9.83 (d, 1H), 9.81-9.76 (d, 1H), 8.01 (dt, J=5.8 Hz, 1H), 7.64-7.57 (m, 3H), 7.52-7.32 (m, 4H), 5.54-5.46 (m, 1H), 5.31-5.22 (m, 1H), 4.55-4.30 (m, 1H), 3.72-3.65 (two singlets, 3H), 2.56 (t, J=7.0 Hz, 3H), 2.46-1.99 (m, 7H). Analytical HPLC (Method A): RT=6.3 min.

Example 23 (Z-Enantiomer 1), Example 24 (Z-Enantiomer 2), Example 25 (E-Enantiomer 1), and Example 26 (E-Enantiomer 2)

(Z)-Methyl N-[8-({2-[5-chloro-2-(1H-1,2,3,4-tetrazol-1-yl)phenyl]ethyl}carbamoyl)-2,10-dioxo-1,2,3,4,7,8,9,10-octahydro-1,9-benzodiazacyclododecin-13-yl]carbamate, and (E)-Methyl N-[8-({2-[5-chloro-2-(1H-1,2,3,4-tetrazol-1-yl)phenyl]ethyl}carbamoyl)-2,10-dioxo-1,2,3,4,7,8,9,10-octahydro-1,9-benzodiazacyclododecin-13-yl]carbamate Example 23 and 24

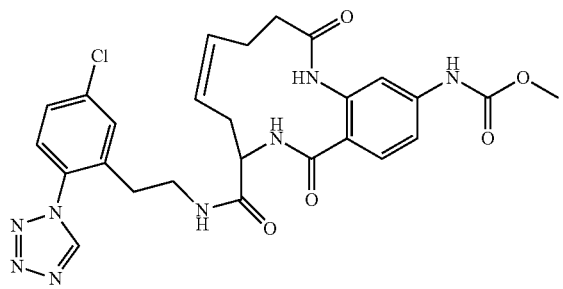

Example 23, Example 24, Example 25 and Example 26: The diastereomeric mixture Example 22 was separated by chiral Prep. SFC to give Example 23, Example 24, Example 25 and Example 26 as single enantiomers.

Example 23: Z-Enantiomer 1 (the first eluting enantiomer), $^1$H NMR (400 MHz, DMSO-$d_6$) δ 9.96 (s, 1H), 9.79 (s, 1H), 8.12 (br. s., 1H), 5.64-5.44 (m, 1H), 5.29-5.11 (m, 1H), 4.63-4.42 (m, 1H), 3.69 (s, 3H), 3.24-3.09 (m, 4H), 2.41-2.11 (m, 6H). MS(ESI) m/z: 567.2 (M+H)+. Analytical HPLC (Method B): RT=4.3 min.

Example 24: Z-Enantiomer 2 (the second eluting enantiomer), 1H NMR (400 MHz, DMSO-$d_6$) δ 9.96 (s, 1H), 9.79 (s, 1H), 8.12 (br. s., 1H), 5.64-5.44 (m, 1H), 5.29-5.11 (m, 1H), 4.63-4.42 (m, 1H), 3.69 (s, 3H), 3.24-3.09 (m, 4H), 2.41-2.11 (m, 6H). MS(ESI) m/z: 567.2 (M+H)+. Analytical HPLC (Method B): RT=4.3 min.

Example 25: E-Enantiomer 1 (the third eluting enantiomer), $^1$H NMR (400 MHz, DMSO-$d_6$) δ 9.82 (s, 1H), 9.73 (s, 1H), 9.26 (s, 1H), 7.91 (t, J=5.9 Hz, 1H), 7.63-7.21 (m, 7H), 5.41 (d, J=7.3 Hz, 1H), 5.24-5.11 (m, 1H), 4.31-4.18 (m, 1H), 3.60 (s, 3H), 3.17-2.99 (m, 4H), 2.37-1.92 (m, 6H). MS(ESI) m/z: 567.2 (M+H)+. Analytical HPLC (Method A): RT=6.5 min.

Example 26: E-Enantiomer 2 (the fourth eluting enantiomer), $^1$H NMR (400 MHz, DMSO-$d_6$) δ 9.82 (s, 1H), 9.73 (s, 1H), 9.26 (s, 1H), 7.91 (t, J=5.9 Hz, 1H), 7.63-7.21 (m, 7H), 5.41 (d, J=7.3 Hz, 1H), 5.24-5.11 (m, 1H), 4.31-4.18 (m, 1H), 3.60 (s, 3H), 3.17-2.99 (m, 4H), 2.37-1.92 (m, 6H). MS(ESI) m/z: 567.2 (M+H)+. Analytical HPLC (Method A): RT=6.5 min.

Example 27

(E/Z)-(±)-N-{2-[5-Chloro-2-(1H-1,2,3,4-tetrazol-1-yl)phenyl]ethyl}-2,10-dioxo-1,2,3,4,7,8,9,10-octahydro-1,9-benzodiazacyclododecine-8-carboxamide Example 25 and 26

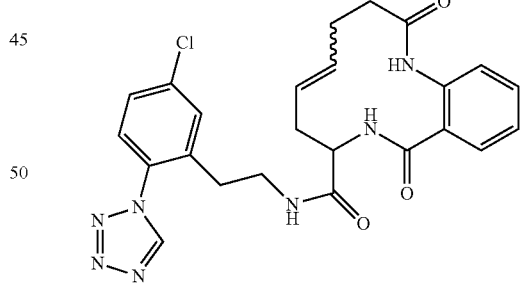

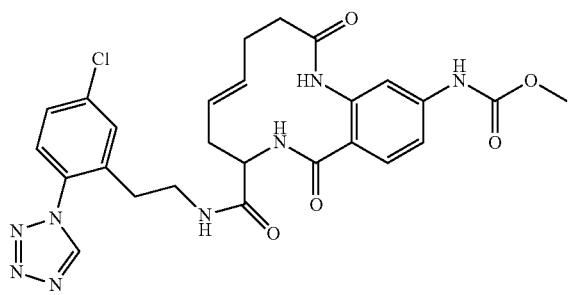 [SMILES: COC(=O)Nc1ccc2c(c1)NC(=O)CCC=CCC(C(=O)NCCc1cc(Cl)ccc1-n1cnnn1)NC2=O]

Example 27 was prepared using a procedure analogous to Example 1 except that 2-amino-4-nitrobenzoic acid was replaced with 2-aminobenzoic acid in step 1B. $^1$H NMR (500 MHz, DMSO-$d_6$) δ 9.81 (br. s., 1H), 9.22 (br. s., 1H), 7.98 (br. s., 1H), 7.73 (d, J=7.2 Hz, 1H), 7.66-7.54 (m, 3H), 7.50-7.38 (m, 2H), 7.36-7.19 (m, 2H), 5.50 (br. s., 1H), 5.37-5.18 (m, 1H), 4.39 (br. s., 1H), 3.22 (br. s., 2H), 2.57 (br. s., 4H), 2.47-2.00 (m, 6H). MS(ESI) m/z: 494.0 (M+H)+. Analytical HPLC (Method D): RT=1.3 min.

Example 28

(±)-N-{2-[5-Chloro-2-(1H-1,2,3,4-tetrazol-1-yl)phenyl]ethyl}-2,10-dioxo-1,2,3,4,5,6,7,8,9,10-decahydro-1,9-benzodiazacyclododecine-8-carboxamide

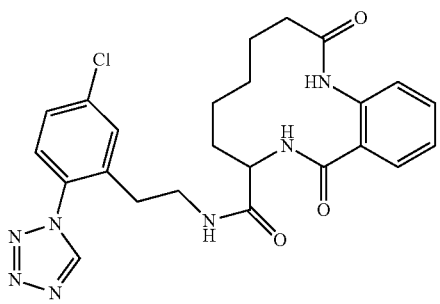 [SMILES: O=C1CCCCCC(C(=O)NCCc2cc(Cl)ccc2-n2cnnn2)NC(=O)c2ccccc2N1]

Example 28: A suspension of Example 27 (6 mg, 0.012 mmol) in MeOH (25 mL) was sonicated, then the flask was evacuated and refilled with Ar (3×), and $PtO_2$ (0.276 mg, 1.215 μmol) was added. The flask was evacuated and refilled with $H_2$ (3×), then stirred at rt under $H_2$ (1 atm). LCMS showed that the reaction was complete. The reaction mixture was concentrated, then dissolved in DMF, filtered, and purified by prep HPLC to give Example 28 (5.1 mg, 81%). $^1$H NMR (500 MHz, DMSO-$d_6$) δ 9.79 (s, 1H), 9.74-9.60 (m, 1H), 8.00 (s, 1H), 7.70-7.51 (m, 3H), 7.51-7.42 (m, 2H), 7.37-7.26 (m, 1H), 7.23-7.12 (m, 1H), 4.37-4.15 (m, 1H), 3.25-3.10 (m, 2H), 2.62-2.54 (m, 2H), 2.42-2.31 (m, 1H), 2.27-2.15 (m, 1H), 1.80-1.55 (m, 3H), 1.53-1.27 (m, 5H). MS(ESI) m/z: 496.2 (M+H)$^+$. Analytical HPLC (Method D): RT=1.3 min.

Example 29

(E/Z)-(±)-N-[(1-Carbamimidoylpiperidin-4-yl)methyl]-2,10-dioxo-1,2,3,4,7,8,9,10-octahydro-1,9-benzodiazacyclododecine-8-carboxamide

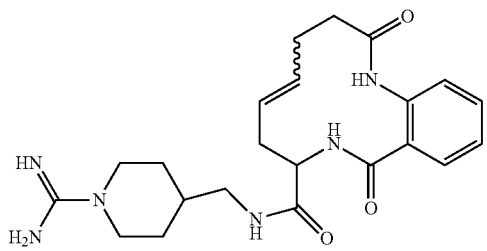 [SMILES: N=C(N)N1CCC(CNC(=O)C2CC=CCCC(=O)Nc3ccccc3C(=O)N2)CC1]

Example 29 was prepared using a procedure analogous to Example 5. $^1$H NMR (500 MHz, DMSO-$d_6$) δ 9.27 (s, 1H), 7.95-7.86 (m, 1H), 7.79-7.66 (m, 1H), 7.52-7.40 (m, 2H), 7.34 (s, 5H), 5.75-5.48 (m, 1H), 5.44-5.25 (m, 1H), 4.55-4.33 (m, 1H), 3.90-3.75 (m, 2H), 2.99 (d, J=13.5 Hz, 4H), 2.63-2.54 (m, 1H), 2.45-2.16 (m, 5H), 1.68 (d, J=13.2 Hz, 3H), 1.17-0.99 (m, 2H). MS(ESI) m/z: 427.2 (M+H)$^+$. Analytical HPLC (Method C): RT=0.8 min.

Example 30 (Z-Isomer) and Example 31 (E-Isomer)

(Z)-(±)-N-(1-Carbamimidoylpiperidin-4-yl)-2,10-dioxo-1,2,3,4,7,8,9,10-octahydro-1,9-benzodiazacyclododecine-8-carboxamide, and (E)-(±)-N-(1-Carbamimidoylpiperidin-4-yl)-2,10-dioxo-1,2,3,4,7,8,9,10-octahydro-1,9-benzodiazacyclododecine-8-carboxamide

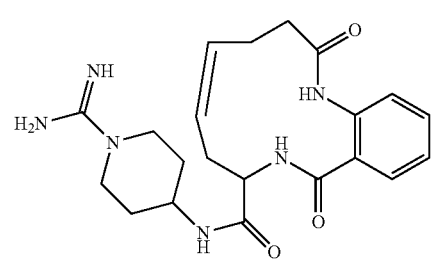

Example 30

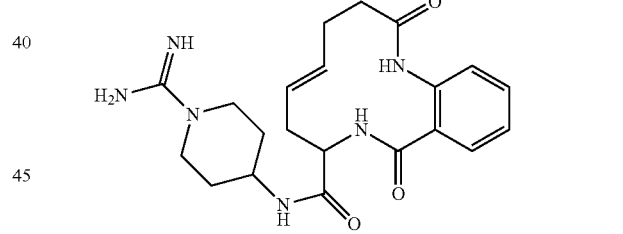

Example 31

Example 30 and Example 31 were prepared using a procedure analogous to Example 4. The E/Z isomers were separated by prep HPLC.

Example 30: $^1$H NMR (500 MHz, DMSO-$d_6$) δ 9.25 (s, 1H), 7.95 (d, J=7.7 Hz, 1H), 7.73 (d, J=8.3 Hz, 1H), 7.50-7.32 (m, 7H), 7.30-7.22 (m, 1H), 5.54 (dd, J=14.7, 7.0 Hz, 1H), 5.37 (dt, J=10.0, 4.8 Hz, 1H), 4.61-4.42 (m, 1H), 3.96-3.68 (m, 3H), 3.16 (t, J=11.6 Hz, 2H), 2.55 (d, J=13.2 Hz, 1H), 2.45-2.13 (m, 5H), 1.81 (dd, J=9.2, 4.0 Hz, 2H), 1.40 (dd, J=13.6, 11.1 Hz, 2H). MS(ESI) m/z: 413.2 (M+H)$^+$. Analytical HPLC (Method D): RT=0.9 min.

Example 31: $^1$H NMR (500 MHz, DMSO-$d_6$) δ 9.83 (br. s., 1H), 8.12 (d, J=7.4 Hz, 1H), 7.57-7.15 (m, 6H), 5.55 (d, J=8.3 Hz, 1H), 5.40-5.24 (m, 1H), 4.66 (br. s., 1H), 4.00-3.72 (m, 2H), 3.15 (t, J=11.6 Hz, 3H), 2.46-2.16 (m, 4H), 1.81 (t, J=9.2 Hz, 2H), 1.46-1.31 (m, 4H). MS(ESI) m/z: 413.2 (M+H)$^+$. Analytical HPLC (Method D): RT=0.9 min.

Example 32

(Z)-(±)-Methyl N-[8-({2-[5-chloro-2-(1H-1,2,3,4-tetrazol-1-yl)phenyl]ethyl}carbamoyl)-4-methyl-2,10-dioxo-1,2,3,4,7,8,9,10-octahydro-1,9-benzodiazacyclododecin-13-yl]carbamate

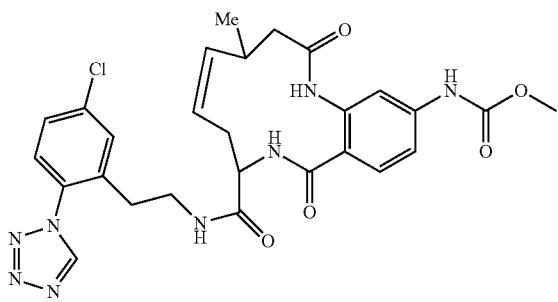 [SMILES: COC(=O)Nc1ccc2c(c1)NC(=O)CC(C)/C=C\CC(C(=O)NCCc1cc(Cl)ccc1-n1cnnn1)NC2=O]

Example 32 was prepared using a procedure analogous to Example 23. $^1$H NMR (500 MHz, DMSO-$d_6$) δ 9.88 (s, 1H), 9.81 (s, 1H), 9.25 (s, 1H), 8.02 (s, 1H), 7.97 (s, 1H), 7.67-7.57 (m, 3H), 7.49 (s, 2H), 7.37 (s, 2H), 5.62 (dd, J=15.5, 7.3 Hz, 1H), 5.38-5.13 (m, 1H), 4.36 (d, J=4.7 Hz, 1H), 3.68 (s, 3H), 3.29-3.11 (m, 2H), 2.63-2.54 (m, 3H), 2.47-2.36 (m, 2H), 2.31-2.22 (m, 1H), 2.21-2.05 (m, 1H), 1.04 (d, J=6.9 Hz, 3H). MS(ESI) m/z: 581.2 (M+H)$^+$. Analytical HPLC (Method D): RT=1.5 min.

Example 33

(E)-(±)-Methyl N-[8-({2-[5-chloro-2-(1H-1,2,3,4-tetrazol-1-yl)phenyl]ethyl}carbamoyl)-4-methyl-2,10-dioxo-1,2,3,4,7,8,9,10-octahydro-1,9-benzodiazacyclododecin-13-yl]carbamate

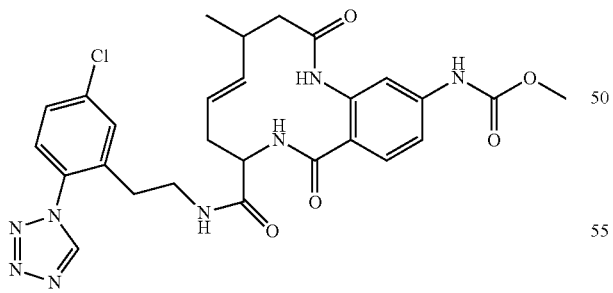

Example 33 was prepared using a procedure analogous to Example 25. $^1$H NMR (400 MHz, DMSO-$d_6$) δ 9.84-9.80 (m, 1H), 9.75-9.71 (m, 1H), 9.34-9.23 (m, 1H), 7.89 (s, 1H), 7.61-7.48 (m, 3H), 7.45-7.35 (m, 2H), 7.27 (d, J=7.0 Hz, 2H), 5.23 (d, J=9.2 Hz, 2H), 4.22 (ddd, J=12.2, 8.1, 4.0 Hz, 1H), 3.61 (s, 3H), 3.17-3.01 (m, 2H), 2.44 (br. s., 4H), 2.35-1.87 (m, 4H), 0.95 (d, J=6.8 Hz, 3H). MS(ESI) m/z: 581.3 (M+H)$^+$. Analytical HPLC (Method A): RT=6.8 min.

Example 34 (Enantiomer 1) and Example 35 (Enantiomer 2)

(E)-Methyl N-[8-({2-[5-chloro-2-(1H-1,2,3,4-tetrazol-1-yl)phenyl]ethyl}carbamoyl)-4-methyl-2,10-dioxo-1,2,3,4,7,8,9,10-octahydro-1,9-benzodiazacyclododecin-13-yl]carbamate

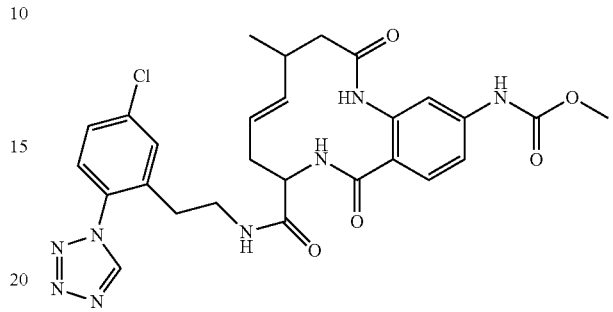

Example 34 and Example 35: Example 33 was separated by chiral Prep. SFC to give Example 34 and Example 35 as the two major single enantiomers.

Example 34: $^1$H NMR (400 MHz, DMSO-$d_6$) δ 9.94-9.83 (m, 1H), 9.80 (s, 1H), 9.33 (s, 1H), 8.00-7.91 (m, 1H), 7.59 (s, 3H), 7.52-7.43 (m, 2H), 7.39-7.23 (m, 2H), 5.32 (d, J=9.2 Hz, 1H), 5.26-5.13 (m, 1H), 4.30 (ddd, J=12.2, 8.1, 4.3 Hz, 1H), 3.26-3.10 (m, 2H), 2.59-2.53 (m, 3H), 2.45-2.38 (m, 1H), 2.35-2.28 (m, 1H), 2.25-2.14 (m, 1H), 2.11-1.97 (m, 1H), 1.03 (d, J=6.8 Hz, 3H). MS(ESI) m/z: 581.2 (M+H)$^+$. Analytical HPLC (Method A): RT=6.9 min.

Example 35: $^1$H NMR (400 MHz, DMSO-$d_6$) δ 9.94-9.83 (m, 1H), 9.80 (s, 1H), 9.33 (s, 1H), 8.00-7.91 (m, 1H), 7.59 (s, 3H), 7.52-7.43 (m, 2H), 7.39-7.23 (m, 2H), 5.32 (d, J=9.2 Hz, 1H), 5.26-5.13 (m, 1H), 4.30 (ddd, J=12.2, 8.1, 4.3 Hz, 1H), 3.26-3.10 (m, 2H), 2.59-2.53 (m, 3H), 2.45-2.38 (m, 1H), 2.35-2.28 (m, 1H), 2.25-2.14 (m, 1H), 2.11-1.97 (m, 1H), 1.03 (d, J=6.8 Hz, 3H). MS(ESI) m/z: 581.2 (M+H)$^+$. Analytical HPLC (Method A): RT=6.9 min.

What is claimed is:
1. A compound of Formula (I):

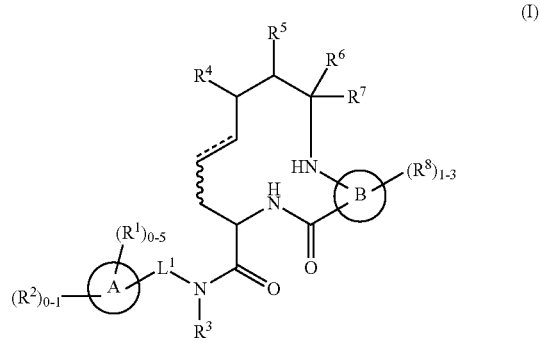

or a stereoisomer, a tautomer, a pharmaceutically acceptable salt thereof, wherein:
 ---- is an optional bond;
 ring A is independently selected from a $C_{3-10}$ carbocycle and a 5- to 10-membered heterocycle comprising: carbon atoms and 1-4 heteroatoms selected from N, NH, N($C_{1-4}$ alkyl), NC(=NH)NH$_2$, O, and S;

ring B is 6-membered aryl;

$L^1$ is independently selected from a bond, —$CR^5R^5$—, —$CHR^5CHR^5$—, —$CR^5$=$CR^5$—, —C≡C—, —$OCH_2$—, —$CHR^5NH$—, —$CH_2O$—, —$SCH_2$—, —$SO_2CH_2$—, and —$CH_2NH$—;

$R^1$ is, independently at each occurrence, selected from halogen, $C_{1-6}$ alkyl, $C_{1-4}$ alkoxy, $C_{1-4}$ alkylthio, $C_{1-4}$ haloalkyl, OH, =O, $OCH_2F$, $OCHF_2$, $OCF_3$, $CF_3$, CN, $NH_2$, $NH(C_{1-4}$ alkyl), $N(C_{1-4}$ alkyl$)_2$, $CO_2(C_{1-4}$ alkyl), $CO(C_{1-4}$ alkyl), —$CH_2NH_2$, —$CONH_2$, —$CONH(C_{1-4}$ alkyl), —$OCH_2CO_2H$, —$NHCO(C_{1-4}$ alkyl), —$NHCO_2(C_{1-4}$ alkyl), —$NHSO_2(C_{1-4}$ alkyl), —$SO_2NH_2$, and —C(=NH)$NH_2$;

$R^2$ is a 5- to 7-membered heterocycle comprising carbon atoms and 1-4 heteroatoms selected from N, NH, $N(C_{1-4}$ alkyl), O, and $S(O)_2$, wherein said heterocycle is substituted with 0-2 $R^{2a}$;

$R^{2a}$ is, independently at each occurrence, selected from halogen, $C_{1-4}$ alkyl, —$CH_2OH$, $C_{1-4}$ alkoxy, OH, $CF_3$, $OCF_3$, $OCH_2F$, $OCHF_2$, CN, $NH_2$, $CO_2H$, $CO_2(C_{1-4}$ alkyl), $COC_{1-4}$ alkyl, —$CONH_2$, —$CONH(C_{1-4}$ alkyl), —$CON(C_{1-4}$ alkyl$)_2$, —$SO_2(C_{1-4}$ alkyl), —$SO_2NH_2$, —$SO_2NH(C_{1-4}$ alkyl), and —$SO_2N(C_{1-4}$ alkyl$)_2$;

$R^3$ is independently selected from H and $C_{1-4}$ alkyl;

alternatively, $L^1$ and $R^3$, together with the nitrogen atom to which they are attached, form a ring;

$R^4$ is selected from H, $C_{1-4}$ alkyl, hydroxyl, F, $CF_3$, and $C_{3-6}$ cycloalkyl;

$R^5$ is selected from H and $C_{1-4}$ alkyl;

$R^6$ is selected from H, halogen, C(O)OH, and C(O)O($C_{1-4}$ alkyl);

$R^7$ is selected from H, $C_{1-4}$ alkyl, and $CF_3$;

alternatively, $R^6$ and $R^7$ together are =O; and $R^8$ is, independently at each occurrence, selected from H, halogen, $NHCO_2C_{1-4}$ alkyl, CN, OH, O—$C_{1-4}$ alkyl, $CF_3$, —$OCF_3$, —$OCHF_2$, —$CHF_2$, —$CH_2F$, $CO_2H$, $CO_2(C_{1-4}$ alkyl), —$CH_2CO_2H$, —$(CH_2)_2CO_2H$, —$CH_2CO_2(C_{1-4}$ alkyl), —$(CH_2)_2CO_2(C_{1-4}$ alkyl), $NH_2$, —$CH_2NH_2$, —$NHCO(C_{1-4}$ alkyl), —$NHCO_2(CH_2)_{1-2}O(C_{1-4}$ alkyl), —$NHCO_2(CH_2)_{1-3}O(C_{1-4}$ alkyl), $NHCO_2CH_2CH(C_{1-4}$ alkyl)O($C_{1-4}$ alkyl), —$NHCO_2(CH_2)_{1-2}OH$, —$NHCO_2CH_2CO_2H$, —$CH_2NHCO_2(C_{1-4}$ alkyl), —$NHC(O)NH(C_{1-4}$ alkyl), —$NHC(O)N(C_{1-4}$ alkyl$)_2$, $NHC(O)NH(C_{1-4}$ alkyl)N(5- to 6-membered heterocycle), —$NHSO_2(C_{1-4}$ alkyl), —$CONH_2$, —$CONH(C_{1-4}$ alkyl), —$CON(C_{1-4}$ alkyl$)_2$, and —$CH_2CONH_2$.

2. The compound of claim 1 having Formula (II):

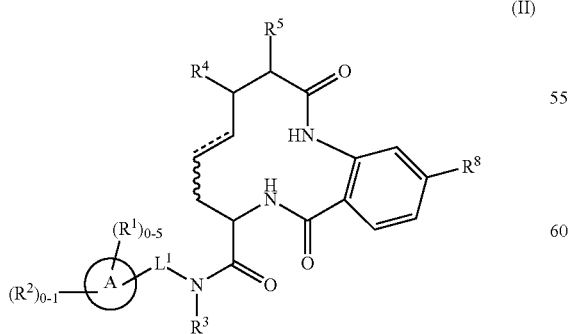

(II)

or a stereoisomer, a tautomer, a pharmaceutically acceptable salt thereof, wherein:

---- is an optional bond;

ring A is independently selected from a $C_{3-10}$ carbocycle and a 5- to 10-membered heterocycle comprising: carbon atoms and 1-4 heteroatoms selected from N, NH, $N(C_{1-4}$ alkyl), NC(=N)$NH_2$, and S;

$L^1$ is independently selected from a bond, —$CR^5R^5$—, and —$CHR^5CHR^5$—;

$R^1$ is, independently at each occurrence, selected from halogen, $C_{1-6}$ alkyl, $C_{1-4}$ alkoxy, $C_{1-4}$ alkylthio, $C_{1-4}$ haloalkyl, OH, =O, $OCH_2F$, $OCHF_2$, $OCF_3$, CN, $NH_2$, $NH(C_{1-4}$ alkyl), $N(C_{1-4}$ alkyl$)_2$, $CO_2(C_{1-4}$ alkyl), $CO(C_{1-4}$ alkyl), —$CH_2NH_2$, —$CONH_2$, —$CONH(C_{1-4}$ alkyl), —$OCH_2CO_2H$, —$NHCO(C_{1-4}$ alkyl), —$NHCO_2(C_{1-4}$ alkyl), —$NHSO_2(C_{1-4}$ alkyl), —$SO_2NH_2$, and —C(=NH)$NH_2$;

$R^2$ is a 5- to 7-membered heterocycle comprising carbon atoms and 1-4 heteroatoms selected from N, NH, and $N(C_{1-4}$ alkyl);

$R^3$ is independently selected from H and $C_{1-4}$ alkyl;

alternatively, $L^1$ and $R^3$, together with the nitrogen atom to which they are attached, form a ring;

$R^4$ is selected from H, $C_{1-4}$ alkyl, hydroxyl, and $C_{3-6}$ cycloalkyl;

$R^5$ is selected from H and $C_{1-4}$ alkyl; and $R^8$ is independently selected from H, halogen, $NHCO_2C_{1-4}$ alkyl, CN, OH, O—$C_{1-4}$ alkyl, $CF_3$, —$OCF_3$, —$OCHF_2$, —$CHF_2$, —$CH_2F$, $CO_2H$, $CO_2(C_{1-4}$ alkyl), —$CH_2CO_2H$, —$(CH_2)_2CO_2H$, —$CH_2CO_2(C_{1-4}$ alkyl), —$(CH_2)_2CO_2(C_{1-4}$ alkyl), $NH_2$, —$CH_2NH_2$, —$NHCO(C_{1-4}$ alkyl), —$NHCO_2(CH_2)_{1-2}O(C_{1-4}$ alkyl), —$NHCO_2(CH_2)_{1-3}O(C_{1-4}$ alkyl), $NHCO_2CH_2CH(C_{1-4}$ alkyl)O($C_{1-4}$ alkyl), —$NHCO_2(CH_2)_{1-2}OH$, —$NHCO_2CH_2CO_2H$, —$CH_2NHCO_2(C_{1-4}$ alkyl), —$NHC(O)NH(C_{1-4}$ alkyl), —$NHC(O)N(C_{1-4}$ alkyl$)_2$, $NHC(O)NH(C_{1-4}$ alkyl)N[5- to 6-membered heterocycle)], —$NHSO_2(C_{1-4}$ alkyl), —$CONH_2$, —$CONH(C_{1-4}$ alkyl), —$CON(C_{1-4}$ alkyl$)_2$, and —$CH_2CONH_2$.

3. The compound of claim 2 having Formula (III):

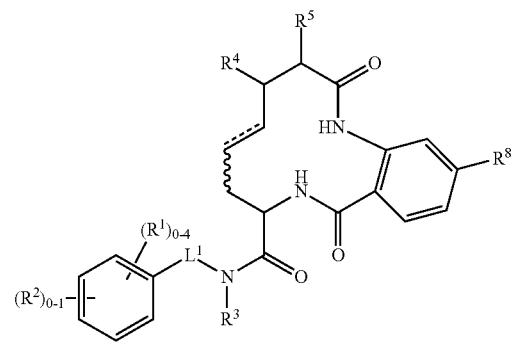

(III)

or a stereoisomer, a tautomer, a pharmaceutically acceptable salt thereof, wherein:

---- is an optional bond;

$L^1$ is independently selected from a bond, —$CR^5R^5$—, and —$CHR^5CHR^5$—;

$R^1$ is, independently at each occurrence, selected from halogen, $C_{1-6}$ alkyl, $C_{1-4}$ alkoxy, $C_{1-4}$ alkylthio, $C_{1-4}$ haloalkyl, OH, =O, $OCH_2F$, $OCHF_2$, $OCF_3$, CN, $NH_2$, $NH(C_{1-4}$ alkyl), and $N(C_{1-4}$ alkyl$)_2$;

61

R² is a 5- to 7-membered heterocycle comprising carbon atoms and 1-4 heteroatoms selected from N and NH;

R³ is independently selected from H and $C_{1-4}$ alkyl;

R⁴ is selected from H, $C_{1-4}$ alkyl, hydroxyl, and $C_{3-6}$ cycloalkyl;

R⁵ is selected from H and $C_{1-4}$ alkyl; and

R⁸ is independently selected from H, halogen, $NHCO_2C_{1-4}$ alkyl, CN, OH, O—$C_{1-4}$ alkyl, $CF_3$, —$OCF_3$, —$OCHF_2$, —$CHF_2$, —$CH_2F$, $CO_2H$, and $CO_2(C_{1-4}$ alkyl).

4. The compound of claim 3 having Formula (IV):

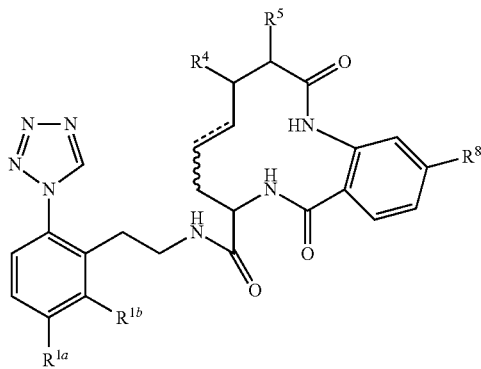

(IV)

or a stereoisomer, a tautomer, a pharmaceutically acceptable salt thereof, wherein:

---- is an optional bond;

$R^{1a}$ is selected from H, F, and Cl;

$R^{1b}$ is selected from H and F;

R⁴ is selected from H, $C_{1-4}$ alkyl, and hydroxyl;

R⁵ is selected from H and $C_{1-4}$ alkyl; and

R⁸ is independently selected from H, halogen, $NHCO_2C_{1-4}$ alkyl, CN, OH, O—$C_{1-4}$ alkyl, $CF_3$, —$OCF_3$, —$OCHF_2$, —$CHF_2$, —$CH_2F$, $CO_2H$, and $CO_2(C_{1-4}$ alkyl).

5. The compound of claim 2, or a stereoisomer, a tautomer, a pharmaceutically acceptable salt thereof, wherein:

---- is an optional bond;

ring A is a 5- to 10-membered heterocycle comprising: carbon atoms and 1-4 heteroatoms selected from N, NH, N($C_{1-4}$ alkyl), and NC(=NH)$NH_2$;

L¹ is independently selected from a bond, —$CR^5R^5$—, and —$CHR^5CHR^5$—;

R¹ is, independently at each occurrence, selected from halogen, $C_{1-6}$ alkyl, and =O;

R³ is independently selected from H and $C_{1-4}$ alkyl;

R⁴ is selected from H, $C_{1-4}$ alkyl, hydroxyl, and $C_{3-6}$ cycloalkyl;

R⁵ is selected from H and $C_{1-4}$ alkyl; and

R⁸ is independently selected from H, halogen, and $NHCO_2C_{1-4}$ alkyl.

6. The compound of claim 5, or a stereoisomer, a tautomer, a pharmaceutically acceptable salt thereof, wherein:

L¹ is independently selected from a bond, —CH—, and —$CH_2CH_2$—;

62 ring A is a 5- to 10-membered heterocycle selected from

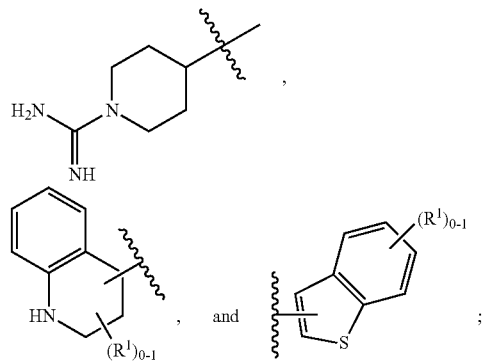

and

R¹ is, independently at each occurrence, selected from halogen and =O.

7. The compound of claim 2, or a stereoisomer, a tautomer, a pharmaceutically acceptable salt thereof, wherein:

---- is an optional bond;

ring A is phenyl;

R¹ is, independently at each occurrence, selected from halogen, $C_{1-6}$ alkyl, $C_{1-4}$ alkoxy, $C_{1-4}$ haloalkyl, and OH;

L¹ and R³, together with the nitrogen atom to which they are attached, form a ring;

R⁴ is selected from H, $C_{1-4}$ alkyl, hydroxyl, and $C_{3-6}$ cycloalkyl;

R⁵ is selected from H and $C_{1-4}$ alkyl; and

R⁸ is independently selected from H, halogen, and $NHCO_2C_{1-4}$ alkyl.

8. A compound of claim 1 selected from:

(±)-methyl N-[8-({2-[5-chloro-2-(1H-1,2,3,4-tetrazol-1-yl)phenyl]ethyl}carbamoyl)-2,10-dioxo-1,2,3,4,5,6,7,8,9,10-decahydro-1,9-benzodiazacyclododecin-13-yl]carbamate;

methyl N-[8-({2-[5-chloro-2-(1H-1,2,3,4-tetrazol-1-yl)phenyl]ethyl}carbamoyl)-2,10-dioxo-1,2,3,4,5,6,7,8,9,10-decahydro-1,9-benzodiazacyclododecin-13-yl]carbamate;

methyl N-[8-({2-[5-chloro-2-(1H-1,2,3,4-tetrazol-1-yl)phenyl]ethyl}carbamoyl)-2,10-dioxo-1,2,3,4,5,6,7,8,9,10-decahydro-1,9-benzodiazacyclododecin-13-yl]carbamate;

(±)-methyl N-{8-[(1-carbamimidoylpiperidin-4-yl)carbamoyl]-2,10-dioxo-1,2,3,4,5,6,7,8,9,10-decahydro-1,9-benzodiazacyclododecin-13-yl}carbamate;

(±)-methyl N-(8-{[(1-carbamimidoylpiperidin-4-yl)methyl]carbamoyl}-2,10-dioxo-1,2,3,4,5,6,7,8,9,10-decahydro-1,9-benzodiazacyclododecin-13-yl)carbamate;

(±)-methyl N-(8-{[2-(1-carbamimidoylpiperidin-4-yl)ethyl]carbamoyl}-2,10-dioxo-1,2,3,4,5,6,7,8,9,10-decahydro-1,9-benzodiazacyclododecin-13-yl)carbamate;

(±)-methyl N-{2,10-dioxo-8-[(2-oxo-1,2,3,4-tetrahydroquinolin-3-yl)carbamoyl]-1,2,3,4,5,6,7,8,9,10-decahydro-1,9-benzodiazacyclododecin-13-yl}carbamate;

(±)-methyl N-(8-{[(5-chloro-1-benzothiophen-3-yl)methyl]carbamoyl}-2,10-dioxo-1,2,3,4,5,6,7,8,9,10-decahydro-1,9-benzodiazacyclododecin-13-yl)carbamate;

(±)-methyl N-{8-[3-(3-chlorophenyl)pyrrolidine-1-carbonyl]-2,10-dioxo-1,2,3,4,5,6,7,8,9,10-decahydro-1,9-benzodiazacyclododecin-13-yl}carbamate;

(±)-methyl N-{8-[3-(3-methoxyphenyl)piperidine-1-carbonyl]-2,10-dioxo-1,2,3,4,5,6,7,8,9,10-decahydro-1,9-benzodiazacyclododecin-13-yl}carbamate;

(±)-methyl N-[8-({2-[5-chloro-2-(1H-1,2,3,4-tetrazol-1-yl)phenyl]ethyl}carbamoyl)-4-methyl-2,10-dioxo-1,2,3,4,5,6,7,8,9,10-decahydro-1,9-benzodiazacyclododecin-13-yl]carbamate;

methyl N-[8-({2-[5-chloro-2-(1H-1,2,3,4-tetrazol-1-yl)phenyl]ethyl}carbamoyl)-4-methyl-2,10-dioxo-1,2,3,4,5,6,7,8,9,10-decahydro-1,9-benzodiazacyclododecin-13-yl]carbamate;

(±)-methyl N-[8-({2-[5-chloro-2-(1H-1,2,3,4-tetrazol-1-yl)phenyl]ethyl}carbamoyl)-3-methyl-2,10-dioxo-1,2,3,4,5,6,7,8,9,10-decahydro-1,9-benzodiazacyclododecin-13-yl]carbamate;

methyl N-[8-({2-[5-chloro-2-(1H-1,2,3,4-tetrazol-1-yl)phenyl]ethyl}carbamoyl)-3-methyl-2,10-dioxo-1,2,3,4,5,6,7,8,9,10-decahydro-1,9-benzodiazacyclododecin-13-yl]carbamate;

(E/Z)-(±)-methyl N-[8-({2-[5-chloro-2-(1H-1,2,3,4-tetrazol-1-yl)phenyl]ethyl}carbamoyl)-2,10-dioxo-1,2,3,4,7,8,9,10-octahydro-1,9-benzodiazacyclododecin-13-yl]carbamate;

(Z)-methyl N-[8-({2-[5-chloro-2-(1H-1,2,3,4-tetrazol-1-yl)phenyl]ethyl}carbamoyl)-2,10-dioxo-1,2,3,4,7,8,9,10-octahydro-1,9-benzodiazacyclododecin-13-yl]carbamate;

(E)-methyl N-[8-({2-[5-chloro-2-(1H-1,2,3,4-tetrazol-1-yl)phenyl]ethyl}carbamoyl)-2,10-dioxo-1,2,3,4,7,8,9,10-octahydro-1,9-benzodiazacyclododecin-13-yl]carbamate;

(E/Z)-(±)-N-{2-[5-chloro-2-(1H-1,2,3,4-tetrazol-1-yl)phenyl]ethyl}-2,10-dioxo-1,2,3,4,7,8,9,10-octahydro-1,9-benzodiazacyclododecine-8-carboxamide;

(±)-N-{2-[5-chloro-2-(1H-1,2,3,4-tetrazol-1-yl)phenyl]ethyl}-2,10-dioxo-1,2,3,4,5,6,7,8,9,10-decahydro-1,9-benzodiazacyclododecine-8-carboxamide;

(E/Z)-(±)-N-[(1-carbamimidoylpiperidin-4-yl)methyl]-2,10-dioxo-1,2,3,4,7,8,9,10-octahydro-1,9-benzodiazacyclododecine-8-carboxamide;

(Z)-(±)-N-(1-carbamimidoylpiperidin-4-yl)-2,10-dioxo-1,2,3,4,7,8,9,10-octahydro-1,9-benzodiazacyclododecine-8-carboxamide;

(E)-(±)-N-(1-carbamimidoylpiperidin-4-yl)-2,10-dioxo-1,2,3,4,7,8,9,10-octahydro-1,9-benzodiazacyclododecine-8-carboxamide;

(Z)-(±)-methyl N-[8-({2-[5-chloro-2-(1H-1,2,3,4-tetrazol-1-yl)phenyl]ethyl}carbamoyl)-4-methyl-2,10-dioxo-1,2,3,4,7,8,9,10-octahydro-1,9-benzodiazacyclododecin-13-yl]carbamate;

(E)-(±)-methyl N-[8-({2-[5-chloro-2-(1H-1,2,3,4-tetrazol-1-yl)phenyl]ethyl}carbamoyl)-4-methyl-2,10-dioxo-1,2,3,4,7,8,9,10-octahydro-1,9-benzodiazacyclododecin-13-yl]carbamate; and (E)-methyl N-[8-({2-[5-chloro-2-(1H-1,2,3,4-tetrazol-1-yl)phenyl]ethyl}carbamoyl)-4-methyl-2,10-dioxo-1,2,3,4,7,8,9,10-octahydro-1,9-benzodiazacyclododecin-13-yl]carbamate.

9. A pharmaceutical composition comprising one or more compounds according to claim 1 and a pharmaceutically acceptable carrier or diluent.

10. A method for the treatment and/or prophylaxis of a thromboembolic disorder, comprising: administering to a patient in need thereof a therapeutically effective amount of a compound of claim 1, or a stereoisomer, a tautomer, or a pharmaceutically acceptable salt thereof.

11. A method according to claim 10, wherein the thromboembolic disorder is selected from the group consisting of arterial cardiovascular thromboembolic disorders, venous cardiovascular thromboembolic disorders, and thromboembolic disorders in the chambers of the heart or in the peripheral circulation.

12. A method according to claim 11, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

* * * * *